(12) United States Patent
Engstrand et al.

(10) Patent No.: US 7,714,112 B2
(45) Date of Patent: May 11, 2010

(54) METHOD OF ANTIBODY PURIFICATION

(75) Inventors: Carina Engstrand, Uppsala (SE); Annika Forss, Uppsala (SE); Gunnar Glad, Uppsala (SE); Bo-Lennart Johansson, Uppsala (SE); Hans J. Johansson, Uppsala (SE); Jean-Luc Maloisel, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 4 days.

(21) Appl. No.: 11/577,203

(22) PCT Filed: Oct. 21, 2005

(86) PCT No.: PCT/SE2005/001591

§ 371 (c)(1),
(2), (4) Date: Apr. 13, 2007

(87) PCT Pub. No.: WO2006/043895

PCT Pub. Date: Apr. 27, 2006

(65) Prior Publication Data

US 2007/0259453 A1 Nov. 8, 2007

(30) Foreign Application Priority Data

Oct. 21, 2004 (SE) .................... 0402558
Nov. 26, 2004 (SE) .................... 0402910

(51) Int. Cl.
*C07K 16/00* (2006.01)
*C07K 1/22* (2006.01)

(52) U.S. Cl. ............... 530/390.5; 530/413; 530/415

(58) Field of Classification Search ............. None
See application file for complete search history.

(56) References Cited

U.S. PATENT DOCUMENTS

| | | | |
|---|---|---|---|
| 4,983,722 A | 1/1991 | Bloom et al. | |
| 5,151,350 A | 9/1992 | Colbert et al. | |
| 5,429,746 A | 7/1995 | Shadle et al. | |
| 5,945,520 A | 8/1999 | Burton et al. | |
| 6,428,707 B1 | 8/2002 | Berg et al. | |
| 6,498,236 B1 | 12/2002 | Lihme et al. | |
| 6,602,990 B1 | 8/2003 | Berg | |
| 6,702,943 B1 | 3/2004 | Johansson et al. | |
| 2002/0110495 A1* | 8/2002 | Hunt et al. ............. 422/101 |
| 2002/0187144 A1* | 12/2002 | Welt et al. ............. 424/142.1 |
| 2008/0177048 A1* | 7/2008 | Gagnon ............. 530/413 |

FOREIGN PATENT DOCUMENTS

| | | |
|---|---|---|
| WO | WO84/00773 | 3/1984 |
| WO | WO01/38227 | 5/2001 |
| WO | WO01/38228 | 5/2001 |
| WO | WO02/053252 | 7/2002 |
| WO | WO03/041859 | 5/2003 |
| WO | WO2004/076485 | 9/2004 |
| WO | WO2006/033634 | 3/2006 |
| WO | WO2006/043896 | 4/2006 |

OTHER PUBLICATIONS

Arshady, R. (Sep. 1988). "Styrene Based Polymer Supports Developed by Suspension Polymerization". La Chimica E L'Industria, 70(9), 70-75.

Blank, G. S., Zapata, G., Fahrner, R., Milton, M., Yedinak, C., Knudsen, H. & Schmelzer, C. (2001). "Expanded bed adsorption in the purification fo monoclonal antibodies: a comparison of process alternatives". Bioseparation, 10, 65-71.

Burton, S. C. & Harding, D. R. K. (2001). "Salt-independent adsorption chromatography: new broad-spectrum affinity methods for protein capture". Journal of Biochemical and Biophysical Methods, 49, 275-287.

Habtermariam, A., Watchman, B., Potter, B. S., Palmer, R., Parsons, S., Parkin, A. & Sadler, P. J. (2001). "Control of aminophosphine chelate ring-opening in Pt($\Pi$) and Pd(II) complexes: potential dual-mode anticancer agents". The Royal Society of Chemistry, 1306-1318.

Hansen, M. B., Lihme, A., Spitali, M. & King, D. (1999). "Capture of human Fab fragments by expanded bed adsorption with a mixed mode adsorbent". Bioseparation, 8, 189-193.

Hermanson, G. T., Mallia, A. K., & Smith, P. K. (1992). "Immobilized Affinity Ligand Techniques" (p. 118). San Diego, CA: Academic Press.

(Continued)

*Primary Examiner*—David A Saunders
(74) *Attorney, Agent, or Firm*—Yonggang Ji

(57) ABSTRACT

The present invention relates to a method of separating antibodies from other compound(s) in a liquid sample, wherein a mobile phase comprising said sample is contacted with a multi-modal separation matrix to adsorb undesired compounds while the antibodies remain free in the liquid, wherein the multi-modal separation matrix comprises first groups, which are capable of interacting with negatively charged sites of the target compounds, and second groups, which are capable of at least one interaction other than charge-charge interaction with said target compounds. The invention also relates to a chromatography column packed with the above-described multi-modal separation matrix and a filter having such multi-modal groups adsorbed to its surface.

25 Claims, 20 Drawing Sheets

OTHER PUBLICATIONS

Hjerten, S. (1964). "The Preparation of Agarose Spheres for Chromatography of Molecules and Particles". Biochimica et Biophysica Acta, 79, 393-398.

Johansson, B., Belew, M., Eriksson, S., Glad, G., Lind, O., Maloisel, J. & Norrman, N. (2003). "Preparation and characterization of prototypes for multi-modal separation aimed for capture of positively charged biomolecules at high salt conditions". Journal of Chromatography A, 1016, 35-49.

Karger, B. L., Snyder, L. R. & Horvath, C. (1973). "An Introduction to Separation Science" (p. 42). New York, NY: John Wiley & Sons.

Kaster, M. (Eds.). (2000). "Protein liquid chromatography" (vol. 61, pp. 81-88). Amsterdam and New York: Elsevier.

Knudsen, H. L., Fahrner, R. L., Xu, Y., Norling, L. A. & Blank, G. S. (2001). "Membrane ion-exchange chromatography for process-scale antibody purification". Journal of Chromatography A, 907, 145-154.

Nau, D. R. (Nov. 29, 2004). "Chromatographic Method For The Purification of Therapeutic-Grade Monoclonal Antibodies" (Online), retrieved May 3, 2005 from http://www.jtbaker.com/techlib/documents/8013.html.

* cited by examiner

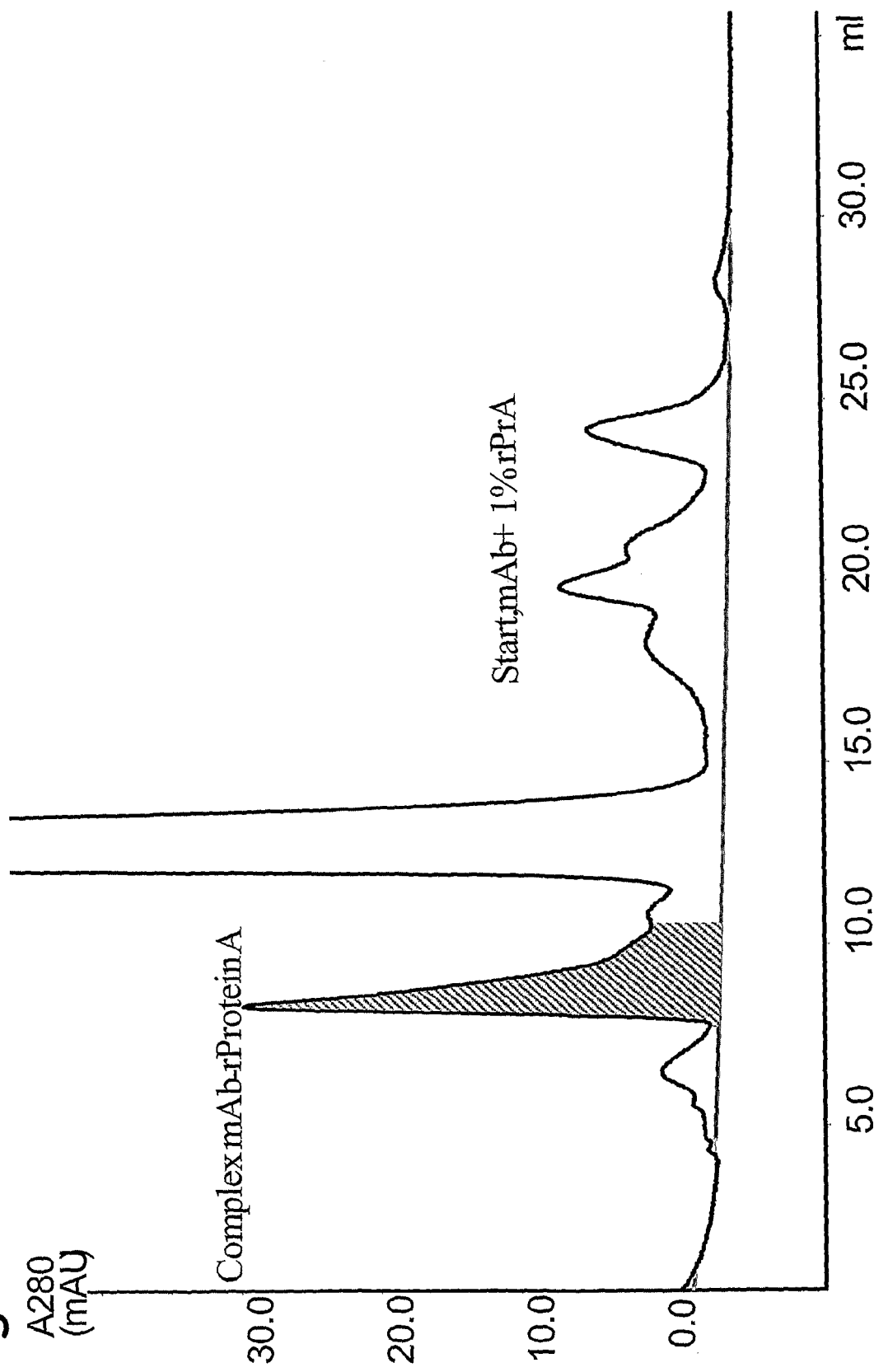

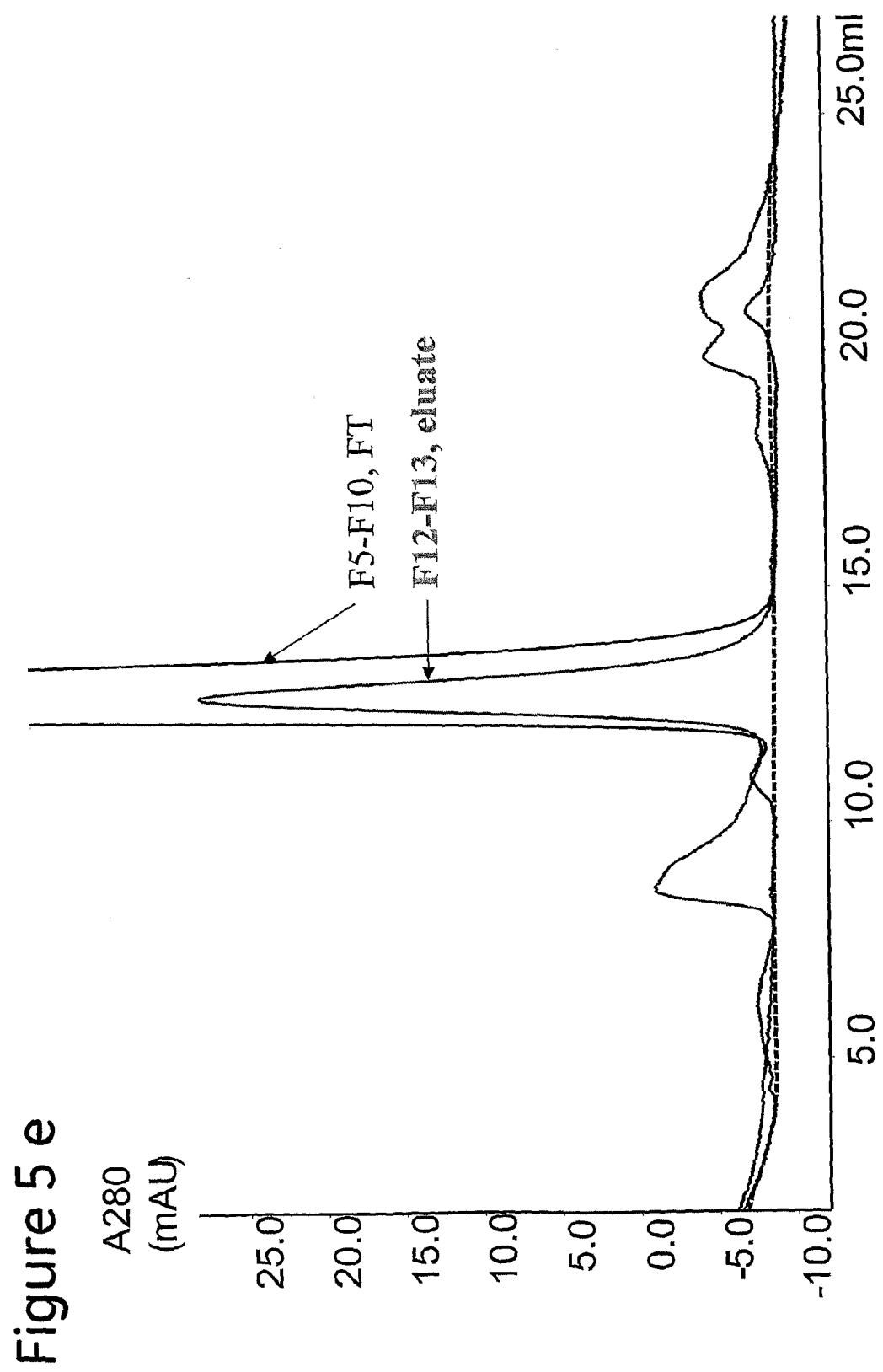

METHOD OF ANTIBODY PURIFICATION

CROSS REFERENCE TO RELATED APPLICATIONS

This application is a filing under 35 U.S.C. §371 and claims priority to international patent application number PCT/SE2005/001591 filed Oct. 21, 2005, published on Apr. 27, 2006, as WO 2006/043895, which claims priority to patent application numbers 0402558-1 filed in Sweden on Oct. 21, 2004 and 0402910-4 filed in Sweden on Nov. 26, 2004.

TECHNICAL FIELD

The present invention relates to a method of purification of antibodies. The method may for example be used on crude feed, or as a step subsequent to affinity chromatography to remove remaining contaminants and substances leaked from the affinity resin. The present invention also encompasses a kit for the purification of antibodies.

BACKGROUND

The immune system is composed of many interdependent cell types that collectively protect the body from bacterial, parasitic, fungal, viral infections and from the growth of tumour cells. The guards of the immune system are macrophages that continually roam the bloodstream of their host. When challenged by infection or immunisation, macrophages respond by engulfing invaders marked with foreign molecules known as antigens. This event, mediated by helper T cells, sets forth a complicated chain of responses that result in the stimulation of B-cells. These B-cells, in turn, produce proteins called antibodies, which bind to the foreign invader. The binding event between antibody and antigen marks the foreign invader for destruction via phagocytosis or activation of the complement system. A number of different classes of antibodies, also known as immunoglobulins, exist, such as IgA, IgD, IgE, IgG, and IgM. They differ not only in their physiological roles but also in their structures. From a structural point of view, IgG antibodies have been extensively studied, perhaps because of the dominant role they play in a mature immune response. Polyclonal antibodies are produced according to standard methods by immunisation of an animal with the appropriate antigen. In response, the animal will produce antibodies which are polyclonal. However, for many purposes, it is desired to have a single clone of a certain antibody, known as monoclonal antibodies. Monoclonal antibodies (MAbs) are produced by hybrid or fused cells comprised of a fusion between a normal B-cell, which produces only a single antibody, to an abnormal myeloma tumour cell. The resulting hybrid, known as a hybridoma, is these days used in standard methods for the production of antibodies.

The biological activity that the immunoglobulins possess is today exploited in a range of different applications in the human and veterinary diagnostic, health care and therapeutic sector. In fact, in the last few years, monoclonal antibodies and recombinant antibody constructs have become the largest class of proteins currently investigated in clinical trials and receiving FDA approval as therapeutics and diagnostics. Complementary to expression systems and production strategies, efficient purification protocols are required to obtain highly pure antibodies in a simple and cost-efficient manner.

Traditional methods for isolation of immunoglobulins are based on selective reversible precipitation of the protein fraction comprising the immunoglobulins while leaving other groups of proteins in solution. Typical precipitation agents are ethanol, polyethylene glycol, lyotropic salts such as ammonium sulphate and potassium phosphate, and caprylic acid. Typically, these precipitation methods are giving very impure products while at the same time being time consuming and laborious. Furthermore, the addition of the precipitating agent to the raw material makes it difficult to use the supernatant for other purposes and creates a disposal problem, which is particularly relevant when speaking of large-scale purification of immunoglobulins.

An alternative method for isolation of immunoglobulins is chromatography, which embraces a family of closely related separation methods. The feature distinguishing chromatography from most other physical and chemical methods of separation is that two mutually immiscible phases are brought into contact wherein one phase is stationary and the other mobile. The sample mixture, introduced into the mobile phase, undergoes a series of interactions with the stationary and mobile phases as it is being carried through the system by the mobile phase. Interactions exploit differences in the physical or chemical properties of the components in the sample. These differences govern the rate of migration of the individual components under the influence of a mobile phase moving through a column containing the stationary phase. Separated components emerge in the order of increasing interaction with the stationary phase. The least retarded component elutes first, the most strongly retained material elutes last. Separation is obtained when one component is retarded sufficiently to prevent overlap with the zone of an adjacent solute as sample components elute from the column. Efforts are continuously being made to design the optimal stationary phase for each specific separation purpose. Such a stationary phase is commonly comprised of a support or base matrix to which a ligand comprising functional i.e. binding groups has been attached. Reference is commonly made to each kind of chromatography based on the principle of interaction it utilises, such as ion-exchange chromatography, hydrophobic interaction chromatography and affinity chromatography.

Ion exchange chromatography is frequently used in protocols for the isolation of immunoglobulins. In anion exchange chromatography, negatively charged amino acid side chains of the immunoglobulin will interact with positively charged ligands of a chromatography matrix. In cation exchange chromatography on the other hand, positively charged amino acid side chains of the immunoglobulin will interact with negatively charged ligands of a chromatography matrix.

Hydrophobic interaction chromatography (HIC) is another method described and used in protocols for the isolation of immunoglobulins. If a highly pure immunoglobulin product is the object, it is commonly recommended to combine HIC with one or more further steps. In HIC, in order to make the immunoglobulin bind efficiently to the HIC matrix, addition of lyotropic salts to the mobile phase is required. The bound immunoglobulin is subsequently released from the matrix by lowering the concentration of lyotropic salt. Thus, a disadvantage of this procedure is the necessity to add lyotropic salt to the raw material, as this may cause problems and a consequently increased cost to the large-scale user. For example, for raw materials such as whey, plasma, and egg yolk, the addition of lyotropic salts to the raw materials would in many instances be prohibitive in large-scale applications, as the salt could prevent any economically feasible use of the immunoglobulin depleted raw material. An additional problem in large-scale applications would be the disposal of several thousand litres of waste.

Affinity chromatography is based on specific interactions between a target biomolecule and a biospecific ligand in a principle of lock-key recognition. Thus, the target and ligand will constitute an affinity pair, such as antigen/antibody, enzyme/receptor etc. Protein-based affinity ligands are well known, such as Protein A and Protein G affinity chromatography which are both widespread methods for isolation and purification of antibodies. It is well known that Protein A chromatography provides an outstanding specificity, particularly towards monoclonal antibodies, and consequently high purities are obtainable. Used in combination with ion exchange, hydrophobic interaction, hydroxyapatite and/or gel filtration steps, Protein A-based methods have become the antibody purification method of choice for many biopharmaceutical companies, see e.g. WO 8400773 and U.S. Pat. No. 5,151,350. However, due to the peptide bonds of the proteins, protein A matrices present a certain degree of alkaline sensitivity. In addition, when Protein A matrices are used to purify antibodies from cell culture media, proteases originating from the cells may cause leakage of Protein A, or peptide fragments thereof.

An attempt to reduce ligand leakage from affinity chromatography matrices has been is presented in WO 03/041859 (Boehlinger Ingelheim Pharma KG), wherein it is suggested to pretreat e.g. Protein A matrices with at least one surfactant to reduce ligand leakage. The affinity matrix may be treated e.g. with 5-15 bed volumes of surfactant. The contact time is crucial for the effectiveness of the process. For example, at room temperature, a contact time of at least 16 h is required for a reduction in leakage.

An alternative approach to the problem of ligand leakage from affinity chromatography matrices is provided in U.S. Pat. No. 4,983,722 (Miles Inc.), wherein Protein A is selectively isolated from a liquid containing antibody and Protein A by exposure thereof to an anion exchange material. Both components are adsorbed to the anion-exchange material, and the antibodies and Protein A are then sequentially eluted under conditions of increasing ionic strength. An illustrative anion exchanger is diethylaminoethyl (DEAE) Trisacryl M or DEAE Sepharose™.

WO 2004/076485 (Lonza Biologics Plc.) relates to antibody purification by Protein A and ion exchange chromatography. The ion exchange step comprises loading the antibody purified on Protein A on an ion exchange material under conditions which allow for the binding of Protein A and collecting the antibody in the flow-through. The anion exchanger is a quaternary amine-based anion exchanger, most preferably Sepharose™ Q (Amersham Biosciences, now GE Healthcare).

U.S. Pat. No. 5,429,746 (SmithKline Beecham Corp.) relates to a process wherein the antibody is first adsorbed to a Protein A chromatographic support and eluted; then adsorbed to a cation exchange chromatographic support and selectively eluted there from; and finally adsorbed to a HIC support and eluted. The mixture applied to the HIC column, following affinity and/or cation exchange chromatography, may contain immunoglobulin aggregates, misfolded species, host cell proteins and residue material from the affinity chromatography step.

U.S. Pat. No. 6,498,236 (Upfront Chromatography) is directed to specific problems caused by small differences in molecular weight between protein-based affinity ligands and target immunoglobulins. Thus, a method is disclosed for the isolation or purification of immunoglobulins from a solution, such as a hybridoma cell culture supernatant, animal plasma or ser, which method is suggested as an alternative to the use of Protein A, Protein G, synthetic peptides and other relatively high molecular weight ligands. The solid phase matrices used in the disclosed method are defined by the formula M-SP1-X-A-SP2-ACID, wherein M designates the matrix backbone, SP1 designates a spacer, X designates O, S or NH, A designates a mono- or bicyclic optionally substituted aromatic or heteroaromatic moiety, SP2 designates an optional spacer and ACID designates an acidic group. The specific substituents are stated to be decisive as to whether the matrix will be binding immunoglobulins efficiently.

U.S. Pat. No. 5,945,520 (Burton et al) discloses mixed mode chromatographic resins which exhibit a hydrophobic character at the pH of binding and a hydrophilic and/or electrostatic character at the pH of desorption. The resin is specifically designed to bind the target compound from an aqueous solution at both a low and high ionic strength. Thus, the adsorption step utilises HIC, while desorption is based on charge repulsion.

U.S. Pat. No. 6,702,943 (Johansson et al) discloses a method for removal of a target substance from a liquid by adsorption thereof to a matrix carrying a plurality of ligands comprising anion-exchanging groups and a hydrophobic structure. More specifically, the ligands contain an aromatic ring in the proximity of the positively charged anion-exchanging groups. It is stated that inclusion of other groups capable of electron donor-electron acceptor interactions may enhance the strength of the interaction between the substance and the adsorbent. The desired substances are stated to be cells, parts of cells and substances comprising peptide structures. The break-through capacity of the matrix is defined for reference proteins such as bovine serum albumin and IgG. The ligands disclosed are denoted "high salt ligands" due to their capability of adsorbing target substances at high concentrations of salt such as 0.25M NaCl.

Further, WO 01/38228 (Belew et al.) discloses another method for removal of a negatively charged substance from a liquid by binding thereof to a matrix that comprises mixed mode anion-exchanging ligands. Each ligand comprises a positively charged nitrogen and a thioether linkage at a distance of 1-7 atoms from said charged nitrogen. Similar to the above, the desired substances, such as cells, parts of cells and substances comprising peptide structures are adsorbed at salt concentrations in the region of 0.25M NaCl.

Ceramic hydroxyapatite has been suggested as useful for immunoglobulin polishing. More specifically, it has been reported (Chromatography, tech note 2849; S. G. Franklin, Bio-Rad Laboratories, Inc., 2000 Alfred Nobel Drive, Hercules, Calif. 94547 USA) that IgG1 can be resolved from an IgG1-Protein A complex in unfractionated media on CHT ceramic hydroxyapatite (Bio-Rad). More specifically, hydroxyapatite ($Ca_{10}(PO_4)_6(OH)_2$) is a form of calcium phosphate, which has been shown to possess unique separation properties. However, hydroxyapatite-based matrices are also known to involve certain disadvantages. For example, due to Ca-leakage, they are unstable at acidic pH values, and they are sensitive to chelating agents such as EDTA. In addition, it has been shown that it is difficult to develop, and to scale up, a robust and reproducible purification method using hydroxyapatite-based matrices, e.g. because it has been difficult to pack hydroxyapatite, and to maintain the performance in large columns. Finally, there is a risk of alterations of the resin properties caused by metal ion contamination and exchange of calcium ions, which alteration is a serious concern for regulatory authorities.

Johansson et al (Journal of Chromatography A, 1016 (2003) 21-33: "Preparation and characterization of prototypes for multi-modal separation media aimed for capture of negatively charged biomolecules at high salt conditions") describes screening of prototypes of multi-modal ligands for the capture of negatively charged proteins from high conductivity mobile phases. It was found that non-aromatic multimodal anion-exchange ligands based on weak ion-exchange ligands (primary and secondary amines) were optimal for the capture of proteins by adsorption at high salt conditions.

BRIEF DESCRIPTION OF THE INVENTION

One aspect of the present invention is to provide a method of separating antibodies from other components of a liquid, which requires less time and process steps than the prior art methods. This can be achieved by a method wherein the liquid comprising antibodies is contacted with a multi-modal separation matrix, and substantially pure antibodies are recovered in non-binding mode. For example, if the liquid is applied to a chromatography column comprising said matrix, the antibodies are easily recovered from the flow through.

Another aspect of the invention is to provide a method of separating antibodies from other components of a liquid, wherein novel specificities are obtained as compared to prior art methods.

A further aspect of the invention is to provide a method of separating antibodies from other components of a liquid, wherein the clearance of contaminants present in a crude feed such as host cell proteins is improved.

Further aspects and advantages of the invention will appear from the detailed description that follows.

BRIEF DESCRIPTION OF THE DRAWINGS

FIG. 1a shows the prototype multi-modal ligand 2-aminobenzimidazole; FIG. 1b shows the prototype multi-modal ligand thiomicamine; FIG. 1c shows the prototype multi-modal ligand N-benzyl-N-methyl ethanolamine immobilised to a support in the form of a bead; and FIG. 1d shows the prototype multi-modal ligand N,N-dimethylbenzylamine immobilized to a support in the form of a bead. In the experimental part, the prototype ligands were coupled to the 600 agarose matrix Sepharose™ 6 FF.

FIG. 4a thiomicamine, 65 µmol/mL (1282004); FIG. 4b thiomicamine, 128 µmol/mL (1282002); FIG. 4c ref. Q Sepharose™ FF; FIG. 4d 2-aminobenzimidazole, 65 µmol/mL (1282045); FIG. 4e 2-aminobenzimidazole, 146 µmol/mL (1282032); FIG. 4f N-benzyl-N-methylethanolamine, 146 µmol/mL (901035A); and FIG. 4g N,N-dimethylbenzylamine, 175 µmol/mL (901035B).

FIGS. 5a-5h show the results of analytical size exclusion chromatography (SEC) on sample with MAb 1, 1% rPrA and pooled flow-through and eluate fractions from the chromatographic runs in FIG. 4. FT: flow-through.

FIG. 5a shows a sample of 4 mg/mL mAb1, 0.04 mg/mL rPrA giving 1% (w/w);

FIG. 5b shows FT and eluate from FIG. 4a thiomicamine, 65 µmol/mL (1282004);

FIG. 5c shows FT and eluate from FIG. 4b thiomicamine, 128 µmol/mL (1282002);

FIG. 5d shows FT and eluate from FIG. 4c 0 Sepharose™ FF;

FIG. 5e shows FT and eluate from FIG. 4d 2-aminobenzimidazole, 65 µmol/mL (1282045);

FIG. 5f shows FT and eluate from FIG. 4e 2-aminobenzimidazole, 146 µmol/mL (1282032);

FIG. 5g shows FT and eluate from FIG. 4f N-benzyl-N-methylethanolamine, 146 µmol/mL (901035A); and FIG. 5h shows FT and eluate from FIG. 4g N,N-dimethylbenzylamine, 175 µmol/mL (901035B).

DEFINITIONS

Figure 1:
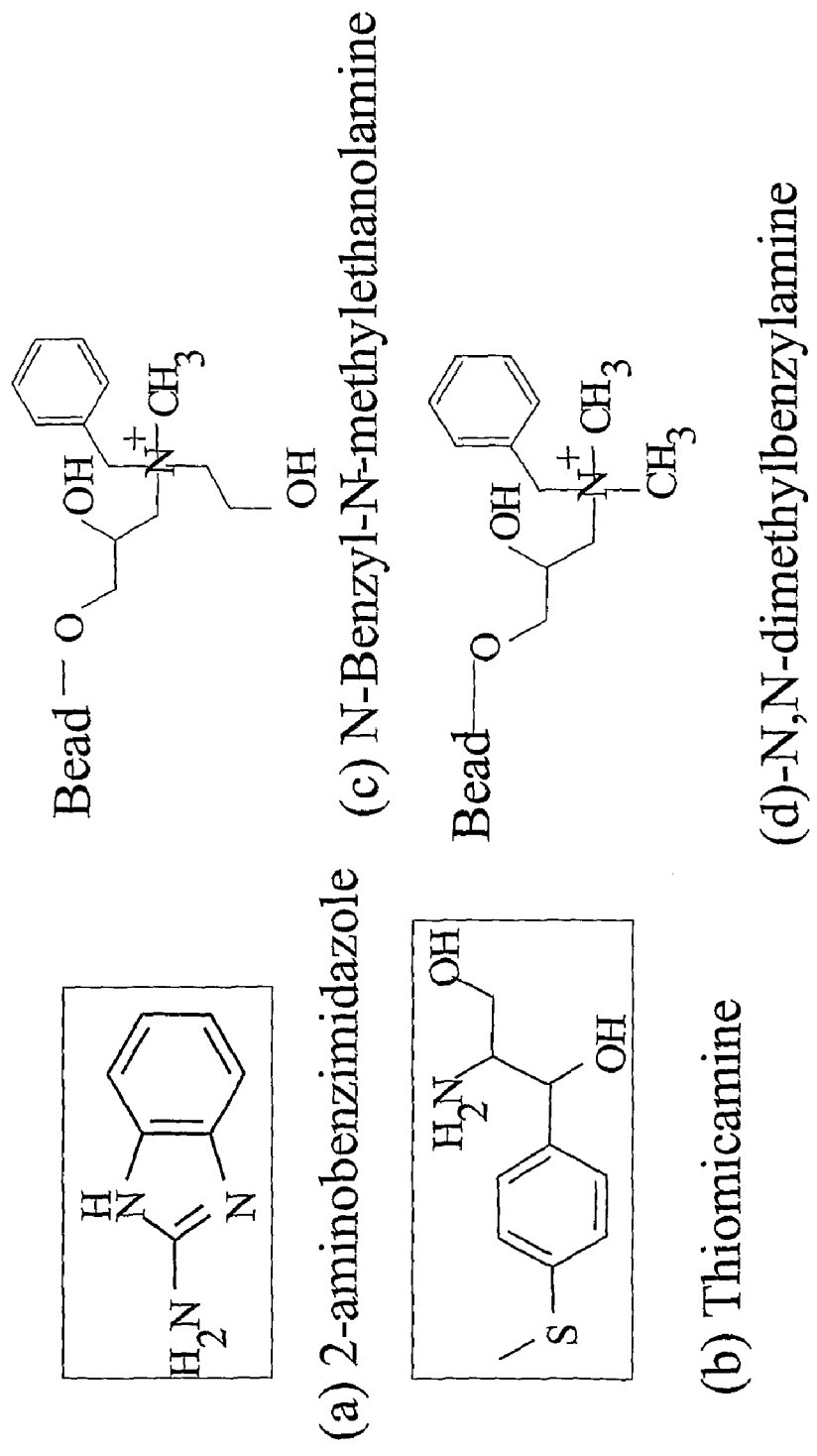
FIGS. 1a-1d show an illustrative selection of multi-modal anion-exchange ligands useful in the method of the present invention: N-benzyl-N-methyl ethanolamine, N,N-dimethylbenzylamine, 2-aminobenzimidazole and thiomicamine.

The terms "antibody" and "immunoglobulin" are used interchangeably in the present specification.

The term "separation matrix" is used herein to denote a material comprised of a support to which one or more ligands comprising functional groups have been coupled.

The term "multi-modal" separation matrix refers to a matrix capable of providing at least two different, but cooperative, sites which interact with the compound to be bound. For example, one of these sites may give an attractive type of charge-charge interaction between the ligand and the substance of interest. The other site may give electron acceptor-donor interaction and/or hydrophobic and/or hydrophilic interactions. Electron donor-acceptor interactions include interactions such as hydrogen-bonding, π-π, cation-π, charge transfer, dipole-dipole, induced dipole etc. "Multi-modal" separation matrices are also known as "mixed mode" separation matrices.

The term "surface" means herein all external surfaces, and includes in the case of a porous support outer surfaces as well as pore surfaces.

The phrase "electron donor-acceptor interactions" means that an electronegative atom with a free pair of electrons acts as a donor and bind to an electron-deficient atom that acts as an acceptor for the electron pair of the donor. (See e.g. Karger et al., An Introduction into Separation Science, John Wiley & Sons (1973) page 42.)

The term "anion exchanging group" means herein a group which is positively charged or chargeable.

The term "eluent" is used in its conventional meaning in this field, i.e. a buffer of suitable pH and/or ionic strength to release one or more compounds from a separation matrix.

The term "capture step" refers in the context of liquid chromatography to the initial step is of a separation procedure. Most commonly, a capture step includes clarification, concentration, stabilisation and a significant purification from soluble impurities. After the capture step, an intermediate purification may follow, which further reduces remaining amounts of impurities such as host cell proteins, DNA, viruses, endotoxins, nutrients, components of a cell culture medium, such as antifoam agents and antibiotics, and product-related impurities, such as aggregates, misfolded species and aggregates.

The term "polishing step" refers in the context of liquid chromatography to a final purification step, wherein trace impurities are removed to leave an active, safe product. Impurities removed during the polishing step are often conformers of the target molecule or suspected leakage products.

The term an "Fc-binding protein" means a protein capable of binding to the crystallisable part (Fc) of an antibody and includes e.g. Protein A and Protein G, or any fragment or fusion protein thereof that has maintained said binding property.

DETAILED DESCRIPTION OF THE INVENTION

In a first aspect, the present invention relates to a method or separating antibodies from one or more other compounds of a liquid sample, wherein a mobile phase comprising said liquid sample is contacted with a multi-modal separation matrix to adsorb one or more target compounds while the antibodies remain free in the mobile phase, wherein the multi-modal separation matrix comprises first groups capable of interacting with negatively charged sites of the target compound(s) and second groups capable of at least one interaction other than charge-charge interaction with said target compound(s). The present invention also encompasses a method wherein third or further groups are added in addition to the first and second groups.

In an advantageous embodiment, the present method is carried out using the principles of liquid chromatography, i.e. by passing a mobile phase over a chromatography column comprising the multi-modal separation matrix. The support may be in the form of porous or non-porous particles, such as essentially spherical particles, a monolith, filter, membrane, surface, capillaries, or any other commonly used format. In an alternative embodiment, the present method is carried out using the principles of expanded bed chromatography i.e. by adding the mobile phase to an expanded bed of separation matrix in the form of particles, such as essentially spherical particles, comprising a high density filler. In another alternative embodiment, the present method is carried out using a batch-wise process, wherein the separation matrix is added to a vessel comprising the liquid sample.

Thus, in the method for the purification of antibodies according to the invention, one or more undesired compounds are adsorbed to the separation matrix while the desired antibodies remain in the mobile phase without being adsorbed. In the context of the present method, it is understood that the term "target" compounds refers to the compounds adsorbed to the separation matrix. Obviously, the nature and identity of the adsorbed compounds will depend on the origin of the liquid sample. Examples of target compounds are cells and cell debris; proteins and peptides; nucleic acids, such as DNA and RNA; endotoxins, and viruses.

In one embodiment of the present invention, the multi-modal separation matrix is provided in a chromatography column and the mobile phase is passed through said column by gravity and/or pumping, the antibodies being recovered in the flow-through of the column. An advantage of the present method is that it does not require any elution of the antibodies from the column. Avoiding a specific elution step is advantageous from a process point of view, since fewer steps will result in a more rapid purification protocol and consequently reduce the process costs. In addition antibodies are sensitive to certain conditions that may impair their folding pattern; or degrade them by attacking their peptide bonds. Even though elution conditions for anion-exchangers in general do not involve any extreme chemicals, every change of salt and pH may affect the sensitive antibody, the effect varying from species to species depending on the pI, charge distribution etc. Consequently, another advantage of the present method is that it avoids adding an eluent and applying eluting conditions to the antibodies.

As mentioned above, in the method according to the invention, the target compounds, from which it is desired to separate the antibodies, are adsorbed to the multi-modal separation matrix. To obtain the most suitable conditions for adsorption of target compounds, the liquid sample is combined with a suitable buffer or other liquid to provide a mobile phase. The present method is advantageously run under conditions conventional for anion-exchange chromatography, which commonly involves adsorption at a relatively low salt concentration. Thus, in one embodiment of the present method, the conductivity of the mobile phase is in the range of 0-25, such as 10-15 mS/cm. In one embodiment, the pH of the mobile phase is about 5-6. The skilled person in this field can easily adapt the conditions to obtain flow-through of the antibodies, e.g. by adjustment of pH or conductivity, which will depend for example on the charge and charge distribution of the antibodies to be purified. If required, one or more washing steps may be applied before or between any such passage(s). If it is desired to subsequently release the adsorbed compounds, e.g. for re-use of the matrix, elution may be carried out at a higher salt concentration, e.g. by use of an increasing salt gradient. The pH value may also or alternatively be shifted, e.g. be a decreasing pH gradient, to elute adsorbed compounds.

As mentioned above, the multi-modal separation matrix comprises first groups, which are capable of interacting with negatively charged sites of the target compounds, and second groups, which are capable of at least one interaction other than charge-charge interaction with said target compounds. In this context, it is understood that the different modes of interaction of groups of the separation matrix are directed to the same target compound, i.e. each target compound is ideally adsorbed by two or more modes of interaction. Multi-modal ligands that comprise positively charged or chargeable anion-exchanging groups are known in this field, see e.g. U.S. Pat. No. 6,702,943 (Johansson et al), WO 01/38228 (Belew et al), and WO 02/053252 (Belew et al).

In one embodiment, the first groups i.e. the anion-exchanging groups of the multi-modal separation matrix are strong anion exchangers. In this context, the term "strong" anion exchangers is understood as groups which remain charged within a wide pH range. In an advantageous embodiment, the strong anion exchanging groups are quaternary amines, is also known as Q groups. In an alternative embodiment, the first groups of the multi-modal separation matrix are weak ion exchangers. In this context, the term "weak" anion exchangers is understood to mean groups that are charged at certain pH values but may loose charge by a pH switch. In a specific embodiment, the first groups comprise a mixture of anion-exchanging groups and additional functionalities, such as anion exchangers and hydrogen-bonding groups. Thus, in this embodiment, the first groups may be TRIS (tris(hydroxymethyl)aminomethane).

In one embodiment, the second groups of the multi-modal separation matrix comprise aromatic groups and/or hydrogen-bonding groups. In one embodiment, said aromatic groups comprise ring systems comprising aromatic or heteroaromatic structures. In an advantageous embodiment, the second groups comprise phenyl groups. Alternatively, the second group may comprise a mixture of aromatic and non-aromatic hydrophobic groups, such as alkyl groups. Thus, in a specific embodiment, the first groups comprise alkyl groups. The separation matrix used according to the invention may comprise two or more functional groups of the same kind, such as two or more different kind of hydrophobic groups; or two or more different kinds of multi-modal anion exchangers.

As understood by the skilled person in this field, the functional groups of the separation matrix used in the present method may be present on the same ligand, in which case each ligand is multi-modal, or on different ligands, in which case the overall nature of the separation matrix is multi-modal.

Thus, in one embodiment, the separation matrix comprises first and second groups coupled to the same ligands. Any one of the above-discussed first and second groups may be used in this embodiment, such as quaternary amine groups and phenyl groups. In one embodiment, the ligands have been coupled to the support via their first groups, such as via amines resulting in quaternary amines. In one embodiment, the first and second groups are distanced from each other by a hydrocarbon chain comprising 1-6, such as 1-3, preferably 1-2 carbon atoms. In a specific embodiment, the ligands are selected from the group consisting of N-benzyl-N-methyl ethanolamine; N,N-dimethylbenzylamine; 2-aminobenzimidazole; thiomicamine; and Q Phenyl.

In an alternative embodiment, the separation matrix comprises first and second groups coupled to different ligands. Any one of the above-discussed first and second groups may be used in this embodiment, such as quaternary amine groups and phenyl groups. In this embodiment, in case of a particulate separation matrix, such different ligands may be immobilised to different or same particles in substantially equal or different amounts. Alternatively, or additionally, a particulate separation matrix may comprise different kinds of first groups; or different kinds of second groups; immobilised onto different particles.

The multi-modal chromatography matrix used in the present method is easily prepared by the skilled person in this field. In brief, the matrix is comprised of ligands coupled to a support, in this field also known as a base matrix, directly or indirectly via a conventional spacer to provide an appropriate distance between the support surface and the interacting groups. To obtain high adsorption capacities, the support is preferably porous, and ligands are then coupled to the external surfaces as well as to the pore surfaces. Methods for immobilisation of ligands to porous or non-porous surfaces are well known in this field; see e.g. Immobilized Affinity Ligand Techniques, Hermanson et al, Greg T. Hermanson, A. Krishna Mallia and Paul K. Smith, Academic Press, INC, 1992. In one embodiment, the ligands density at the surface of the support is in a range close to what is commonly used for conventional ion-exchange matrices. The ligands may be coupled directly to the support simply via the linker element resulting from the chemistry used; or via a longer element known as extender, tentacle or flexible arm, see e.g. U.S. Pat. No. 6,428,707, which is hereby included herein via reference. In brief, the extender may be in the form of a polymer such as a homo- or a copolymer. Hydrophilic polymeric extenders may be of synthetic origin, i.e. with a synthetic skeleton, or of biological origin, i.e. a biopolymer with a naturally occurring skeleton. Typical synthetic polymers are selected from the group consisting of polyvinyl alcohols; polyacryl- and polymethacrylamides; and polyvinyl ethers. Typical biopolymers are selected from the group consisting of polysaccharides, such as starch; cellulose; dextran; and agarose.

The support may be made from an organic or inorganic material. In one embodiment, the support is prepared from a native polymer, such as cross-linked carbohydrate material, e.g. agarose, agar, cellulose, dextran, chitosan, konjac, carrageenan, gellan, alginate etc. The native polymer supports are easily prepared and optionally cross-linked according to standard methods, such as inverse suspension gelation (S Hjertén: Biochim Biophys Acta 79(2), 393-398 (1964). In an especially advantageous embodiment, the support is a kind of relatively rigid but porous agarose, which is prepared by a method that enhances its flow properties, see e.g. U.S. Pat. No. 6,602,990 (Berg) or SE 0402322-2 (Berg et al.) In an alternative embodiment, the support is prepared from a synthetic polymer or copolymer, such as cross-linked synthetic polymers, e.g. styrene or styrene derivatives, divinylbenzene, acrylamides, acrylate esters, methacrylate esters, vinyl esters, vinyl amides etc. Such synthetic polymers are easily prepared and optionally cross-linked according to standard methods, see e.g. "Styrene based polymer supports developed by suspension polymerization" (R Arshady: Chimica e L'Industria 70(9), 70-75 (1988)). Native or synthetic polymer supports are also available from commercial sources, such as GE Healthcare, Uppsala, Sweden, for example in the form of porous particles. In yet an alternative embodiment, the support is prepared from an inorganic polymer, such as silica. Inorganic porous and non-porous supports are well known in this field and easily prepared according to standard methods.

Suitable particle sizes of the present separation matrix may be in the diameter range of 5-500 µm, such as 10-100 µm, e.g. 20-80 µm. In the case of essentially spherical particles, the average particle size may be in the range of 5-1000 µm, such as 10-500. In a specific embodiment, the average particle size is in the range of 10-200 µm. The skilled person in this field can easily choose the suitable particle size and porosity depending on the process to be used. For example, for a large scale process, for economical reasons, a more porous but rigid support may be preferred to allow processing of large volumes, especially for the capture step. In chromatography, process parameters such as the size and the shape of the column will affect the choice. In an expanded bed process, the matrix commonly contains high density fillers, preferably stainless steel fillers. For other processes other criteria may affect the nature of the matrix.

The antibodies separated according to the present invention may originate from any commonly used source, such as cells cultured at a surface or from batch-wise or continuous cell culture in fermentation tanks or vessels. Thus, in one embodiment, the liquid is a supernatant obtained from cell fermentation. Examples of compounds that are adsorbed are proteins, DNA, viruses, endotoxins, nutrients, components of a cell culture medium, such as antifoam agents and antibiotics, and product-related impurities, such as misfolded species and aggregates. The step of contact between the mobile phase and the multi-modal separation matrix, i.e. the adsorption step, may be preceded by a step of mechanical filtration, centrifugation and/or chromatography. For example, if the liquid sample is a fermentation broth, it is advantageous to mechanically remove cell debris, whole cells and other relatively large components before the multi-modal chromatography.

In one embodiment, the present method constitutes the capture step of a purification protocol. In a specific embodiment, the liquid sample is a crude feed which is filtrated before contact with the multi-modal chromatography matrix. Consequently, this embodiment would still constitute a capture step, even though the liquid sample has been prepurified by mechanical means. As is well known, the host cells that produce antibodies will also comprise a number of other proteins commonly known as host cell proteins (HCP). Such HCPs include enzymes, such as proteases, and other proteins produced by the host cells. According to the present invention, it was unexpectedly found that the host cell proteins could be adsorbed to the multi-modal separation matrix while the antibodies remain free in the mobile phase. Thus, in one embodiment, substantially all host cell proteins of the liquid sample are adsorbed to the multi-modal separation matrix.

In alternative embodiments, the present method is used as a second, third or even fourth step in a cleaning protocol, such as an intermediate purification or polishing step. Thus, in one embodiment, the mobile phase applied to the multi-modal separation matrix comprises an antibody-containing eluate from a separation matrix. In one embodiment, the liquid sample is an eluate from a preceding affinity chromatography matrix. In an advantageous embodiment, the separation matrix from which the eluate is obtained comprises one or more Fc-binding protein ligands, such as Protein A ligands. The term protein A ligands includes in this context native as well as recombinant protein A, or functional fragments thereof. In this context, the term "functional" fragment means a fragment that has retained the original binding properties of the protein. Such affinity matrices are commercially available, such as MabSelect™ from GE Healthcare. Consequently, in this embodiment, the adsorbed compounds may be one or more selected from the group that consists of released Protein A; complexes formed between Protein A and antibodies, such as Protein A-MAb complexes, which complexes may comprise a number of antibodies per Protein A molecule, such as 2-4 antibodies complexed with one Protein A molecule; and aggregates of released Protein A or antibodies. As the skilled person in this field will understand, depending on the specific conditions used in the preceding step, such as affinity chromatography, the eluate may need conditioning by suitable additions or adjustment. Thus, the eluate is combined with a suitable buffer or liquid to provide a mobile phase. It is noted that even though it may be preferred for practical reasons, if an eluate from a Protein A column is to be purified, the present method is not necessarily performed directly following the affinity chromatography, or even in the same facilities.

In a specific embodiment, the present method is a multi-step process comprising a capture step on an affinity chromatography matrix such as a Protein A chromatography matrix and a polishing step on a multi-modal separation matrix, as described above. The liquid sample applied to the affinity chromatography matrix may be a cell culture liquid or a fermentation broth, which has optionally been subjected to pretreatment such as filtration and/or conditioning by adjustment of pH and/or conductivity to provide a mobile phase. In this process, the capture step will remove one or more host cell proteins and host cell residues such as cell debris and proteins, DNA, endotoxins, and the like. In the subsequent polishing step, primarily compounds in the form of residues from the capture step, such as Protein A-antibody aggregates, will be adsorbed.

The present method is useful to recover any monoclonal or polyclonal antibody, such as antibodies originating from mammalian hosts, e.g. mice, rodents, primates and humans, or antibodies originating from hybridomas. In one embodiment, the antibodies recovered are human or humanised antibodies. In an advantageous embodiment, the antibodies are monomeric antibodies. The antibodies may be of any class, i.e. selected from the group that consists of IgA, IgD, IgE, IgG, and IgM. In one embodiment, the antibodies to be purified are antibodies capable of binding to Protein A, or Fc-containing antibody fragments or fusion proteins. In a specific embodiment, the antibodies recovered are immunoglobulin G (IgG), such as IgG1. In one embodiment, the present method is used to purify antibodies having a pI in the range of 6-9, such as in the range of 7-8. In a specific embodiment, the pI of the purified antibodies is about 9. In the present context, it is to be understood that the term "antibodies" also includes antibody fragments and any fusion protein that comprises an antibody or an antibody fragment. Thus, the present invention also encompasses the purification of fragments of any one of the above mentioned antibodies as well as fusion proteins comprising such antibodies. In one embodiment, the antibodies are monoclonal antibodies.

As appears from the above, in the present method, undesired compounds are adsorbed to the multimodal separation matrix, and a substantially pure fraction of non-adsorbed antibodies is recovered. In this context, the term "substantially pure" is understood to mean that substantially all the non-antibody compounds have been removed. Most advantageously, at least about 80%, such as at least about 95%, i.e. in the interval of 95-100%, such as at least about 98%, i.e. in the interval of 98-100% and preferably at least about 99%, i.e. in the interval of 99-100%, of the total amount of contaminants is removed on the multi-modal separation matrix. However, as the skilled person in this field will appreciate, the possible purities will depend on the concentration of antibody in the liquid sample applied to the separation matrix as well as other conditions used. Thus, in one embodiment, the antibodies separated according to the present method are antibodies of therapeutic grade. Thus, the antibodies purified according to the invention are useful in research and also for the preparation of antibody pharmaceuticals, such as MAb drugs. An alternative use of the purified antibodies is for diagnostic use. Further, the purified antibodies are also useful in food products such as food additives for humans. For example, bovine antibodies purified according to the present invention are useful in food products.

In a specific embodiment of the present method, the multi-modal separation matrix is provided as a disposable chromatography column or filter. An advantage of using disposable products in a method for purification of therapeutic compounds such as antibodies is that by discarding the separation matrix after use, the risk of cross-contamination between two different processes is eliminated. In many such methods, it is required to maintain aseptic conditions. Thus, in one embodiment of the present method, the multi-modal separation matrix has been sterilized, and the sterile multi-modal separation matrix is provided as a sterile packed chromatography column or a filter. In one embodiment, the present method is carried out as a batch-wise process, wherein a disposable separation multi-modal matrix is added to a vessel comprising the liquid from which the antibodies are to be recovered. In an advantageous embodiment, the disposable separation matrix is then comprised of dried particles, such as dried agarose particles, which easily swell as the contact the aqueous liquid. A suitable time is allowed for target compounds to adsorb to the matrix, after which the liquid phase comprising the antibodies is removed from the vessel. The used matrix may then be disposed of, without releasing the adsorbed compounds, which again may be advantageous from a safety point of view since compounds such as endotoxins; prions and/or certain host cell proteins need not be handled any further.

In a second aspect, the present invention relates to a kit for the purification of antibodies from one or more other components in a liquid, which kit comprises in separate compartments a first chromatography column packed with a first separation matrix; a second chromatography column packed with a multi-modal separation matrix, which comprises first groups capable of interacting with negatively charged sites of the target compounds, and second groups capable of at least one interaction other than charge-charge interaction with said target compounds; one or more buffers; and written instructions. In an advantageous embodiment, the instructions teach the purification of antibodies from the flow-through of a multi-modal separation matrix. The ligands; support and other details of the multi-modal separation matrix may be as described above. The instructions advantageously describe a method as defined above. In one embodiment of the kit, the first separation matrix is an affinity chromatography matrix and preferably comprises protein ligands, such as protein A or G ligands. In another embodiment, the first and/or the second chromatography columns are sterile and/or disposable columns.

Finally, the present invention also relates to a disposable chromatography column for the purification of antibodies, which column comprises a multi-modal separation matrix comprising first groups capable of interacting with negatively charged target sites and second groups capable of at least one interaction other than charge-charge interaction. The ligands; support and other details of the multi-modal separation matrix may be as described above. In one embodiment, the separation matrix is capable of adsorbing proteins other than antibodies from a mobile phase wherein the conductivity is in the range of 0-50, such as 0-25 e.g. 0-15 mS/cm. An alternative embodiment of this aspect is a disposable filter for the purification of antibodies, which filter comprises first groups capable of interacting with negatively charged target sites and second groups capable of at least one interaction other than charge-charge interaction, which groups are coupled to the filter surface. In a specific embodiment, the present filter is capable of adsorbing proteins other than antibodies from a mobile phase wherein the conductivity is in the range of 0-50, such as 0-25 e.g. 0-15 mS/cm.

Experimental Part

The present examples are provided for illustrative purposes only, and should not be interpreted in any way as limiting the scope of the invention as defined by the appended claims. All references provided below and elsewhere in the present specification are hereby included herein via reference.

Disposition

Under non-binding conditions, sample containing approximately 50 mg mAb1 were loaded onto prototypes 901035 A (N-benzyl-N-methyl ethanolamine) and 901035 B (N,N-dimethylbenzylamine) at approximately 5 and 12 mS/cm. Flow-through fractions (FT) were collected at 5, 10 and 15 column volumes (CV). Fractions from the elution peak were pooled. FT fractions were analysed for HCP and Protein A content.

Prototypes with high and low ligand densities were made for the multi-modal ligands 2-aminobenzimidazole and thiomicamine. At pH 6.5, sample containing 20 mg of mAb1 were loaded to the columns at approximately 5 and 12 mS/cm. The performance of the prototypes was first evaluated with analytical SEC. Selected fractions were analysed for is HCP and Protein A content. After screening the fractions with SEC selected fractions were sent for HCP and Protein A analysis.

To confirm that the chromatographic performance was not unique for one particular mAb, the chromatographic runs were repeated using a sample containing mAb2 at pH 6.0 and approximately 12 mS/cm. The performance of the prototypes was first evaluated with analytical SEC. Selected fractions were analysed for HCP and Protein A content. After screening the fractions with SEC selected fractions were sent for HCP and Protein A analysis.

To more easily distinguish which of the prototypes who gave the best rProtein A clearance MAb1 was spiked with 1% (w/w) recombinant Protein A (rPrA). Each prototype was injected with a sample volume corresponding to 10 mg MAb1, 1% rProtein A at pH 6.0 and a conductivity of approximately 7 mS/cm. Flow-through and eluate fractions were pooled separately and analysed with SEC.

Materials/Investigated Units

Columns and gels were obtained from GE Healthcare, Uppsala, Sweden

| | | |
|---|---|---|
| HiPrep ™ 26/10 Desalting | cat.no. 17-5087-01 | CV = 53.09 mL |
| Tricorn ™ 5/50 | cat.no. 18-1163-09 | CV = 1 mL |
| HR 5/5 ™ | cat.no. 18-0338-01 | CV = 1 mL |
| Superdex ™ 200 10/300 GL, | cat.no. 17-5175-01 | CV = 23.56 mL |

Instruments

| | |
|---|---|
| Chromatography systems: | ÄKTAExplorer ™ 10 |
| Spectrophotometer | Spectra MAX plus |

Chemicals

All chemicals used were of analytical grade. Water was MilliQ-filtered.

Chromatography Media

The reference matrix was Q Sepharose™ Fast Flow (FF) (GE Healthcare, Uppsala, Sweden). The multi-modal separation matrix prototypes carried ligands as described in Table 1 below:

TABLE 1

Multimodal anion exchange ligands

| Prototype ref. | Ligand | Cl⁻ capacity (µmol/mL) |
|---|---|---|
| 901035A | N-benzyl-N-methyl ethanolamine | 146 |
| 901035B | N,N-dimethylbenzylamine | 175 |
| 1282002 | thiomicamine | 128 |
| 1282004 | thiomicamine | 65 |
| 1282032 | 2-aminobenzimidazole (ABI) | 146 |
| 1282045 | 2-aminobenzimidazole (ABI) | 65 |

Preparation of Prototype N-Benzyl-N-Methyl Ethanolamine Sepharose™ Fast Flow

A. Introduction of Allyl Group on the Matrix

Sepharose™ 6 Fast Flow (GE Healthcare, Uppsala, Sweden) was activated with allyl glycidyl ether as follows: 100 ml of Sepharose™ 6 Fast Flow was suction dried, mixed with 0.3 g of NaBH$_4$, 12 g of Na$_2$SO$_4$ and 35 ml of 50% aqueous solution of NaOH. The mixture was stirred for 1 hour at 50° C. After addition of 100 ml of allyl glycidyl ether the suspension was left at 50° C. under vigorous stirring for an additional 16 hours. After filtration of the mixture, the gel was washed successively, with 500 ml distilled water, 500 ml ethanol, 200 ml distilled water 200 ml 0.2 M acetic acid and, 500 ml distilled water.

Titration gave a degree of substitution of 0.22 mmol of allyl/ml of gel.

B. Activation of Allyl Sepharose™ 6 Fast Flow Via Bromination

Bromine was added to a stirred suspension of 50 ml of allyl activated Sepharose™ 6 Fast Flow (0.22 mmol allyl groups/ml drained gel), 1 g of sodium acetate and 15 ml of distilled water, until a persistent yellow colour was obtained. Sodium formate was then added until the suspension was fully decolourised. The reaction mixture was filtered and the gel washed with 500 ml of distilled water. The activated gel was then directly transferred to a reaction vessel and further reacted with N-benzyl-N-methylethanolamine.

C. Introduction of BMEA (N-Benzyl-N-Methylethanolamine) Groups on the Activated Matrix The amine groups were introduced on the matrix directly via the nitrogen atom of the amine groups. In a typical procedure, the coupling to the matrix was realised via bromination of the allyl group and nucleophilic substitution under basic conditions. 25 ml of bromine activated gel (0.22 mmol allyl groups/ml drained gel) was transferred to a reaction vial containing a solution of N-benzyl-N-methylethanolamine (16.0 ml). 5 ml of water was added and the pH of the reaction solution was adjusted to 12.0 with sodium hydroxide solution. The reaction was left for 16 hours under stirring at 50° C. After filtration of the reaction mixture the gel was successively washed with 3×10 ml of distilled water, 3×10 ml aqueous 0.5 HCl and finally 3×10 ml of distilled water. BMEA Sepharose™ Fast Flow gel was obtained with a degree of substitution of 0.15 mmol amines/ml of gel.

2-aminobenzimidazole and thiomicamine prototypes with high and low ligand densities were made in accordance with standard procedures (see U.S. Pat. No. 6,702,943 (Johansson et al), WO 01/38228 (Belew et al), and WO 02/053252 (Belew et al)).

Samples

Two different humanised IgG antibodies, subclass 1, denoted MAb 1 and MAb 2, with an extinction coefficient of 1.46 and 1.50 respectively, were used. Both antibodies were expressed in a CHO cultures and subsequently purified using conventional Protein A affinity chromatography prior to the present experiments.

Buffer exchange was made on a HiPrep™ Desalting column (GE Healthcare, Uppsala, Sweden), equilibrated with the buffer of interest, by injecting an appropriate volume (5-15 mL) with a Superloop™ (GE Healthcare, Uppsala, Sweden). The flow rate was 5 mL/min and fractions of 5 mL were collected. Fractions containing the eluted peak were pooled and the absorbance at 280 nm determined in duplicates, in order to calculate the concentration according to equation 1:

$$A_{280} = \epsilon \cdot C \cdot l \quad \text{(Eqn 1)}$$

wherein $A_{280}$ is the absorbance at 280 nm.

$\epsilon (mL*mg^{-1}*cm^{-1})$ is the extinction coefficient for a particular protein.

C (mg/mL) is the concentration of the protein.

l (cm) is the path length.

Size exclusion chromatography (SEC) was performed on a Superdex™ 200 10/300 column (GE Healthcare, Uppsala, Sweden) at a flow rate of 0.5 mL/min. The buffer was PBS (phosphate-buffered saline); 10 mM phosphate, 0.137 M NaCl, 2.7 mM KCl, pH 7.4 prepared from tablets (Sigma, P-4417).

| Method | | | |
|---|---|---|---|
| Equilibration | 2/0.1 CV; | 2 CV first time use; | 0.1 CV between runs |
| Sample injection | 50 µl | | |
| Isocratic Elution | 1.5 CV | | |

Chromatography on Prototypes with mAb

A-buffer was 25 mM Bis-Tris, pH 6.0 or 6.5. Depending on the desired conductivity, approximately 5 or 12 mS/cm, 35 or 100 mM NaCl was included. For prototypes 901035 A and 901035 B, elution buffer (B-buffer) was 25 mM Bis-Tris, 0.5 M NaCl, pH 6.5. For prototypes with thiomicamine and ABI as ligands, elution buffer (B-buffer) was 0.5 M Na-Acetate, pH 4.0. The flow rate was 0.5 mL/min (150 cm/h).

| Method: | | | |
|---|---|---|---|
| Equilibration | | 5 CV | A-buffer |
| Sample injection | | 5-25 | mL sample cont. 20 or 50 mg mAb |
| Wash | | 5 CV | A-buffer |
| Gradient Elution | | 10 CV | 0-100% B-buffer |
| Elution | | 10 CV | 100% B-buffer |
| Regeneration | | 5 CV | A-buffer |

Chromatography on Prototypes with mAb-rProtein A

A-buffer was 25 mM Bis-Tris, pH 6.0. The conductivity was approximately 7 mS/cm by addition of 50 mM NaCl, B-buffer was 0.5 M Na-acetate, pH 4.0. Flow rate was 0.5 mL/min (150 cm/h). Sample concentration was 4 mg/mL MAb 1-0.04 mg/mL rPrA giving 1% (w/w).

| Method: | | | |
|---|---|---|---|
| Equilibration | | 5 CV | A-buffer |
| Sample injection | | 2.5 mL | 10 mg MAb, 1% rPrA |
| Wash | | 5 CV | A-buffer |
| Gradient Elution | | 10 CV | 0-100% B-buffer |
| Elution | | 10 CV | 100% B-buffer |
| Regeneration | | 5 CV | A-buffer |

CIP (Cleaning in Place)

After each chromatographic run, the prototypes and the reference matrix Q Sepharose™ FF were subject to the following CIP procedure;

| | |
|---|---|
| 30% isopropanol | 5 CV (Column Volumes) |
| H$_2$O | 5 CV |
| 1.0 M NaOH | 4 CV (incl. 15 min. pause) |
| H$_2$O | 5 CV |

-continued

| | |
|---|---|
| A-buffer | 5 CV |
| H$_2$O | 5 CV |
| 20% EtOH | 5 CV |

Protein A Analysis

Selected fractions were mixed with SPA sample diluent in proportions of 800 μl SPA sample diluent+200 μl sample. After mixing, the fractions were heated on a heating block at 99° C. for 10 minutes, then mixed again. The samples were then analysed for recombinant Protein A.

Host Cell Proteins (HCP) Analysis

The samples (min. 600 μl) were analysed for HCP content. The lower detection limit is 10 ng/mL.

Example 1

MAb1-Containing Sample Purified on Prototype Ligands N-Benzyl-N-Methylethanolamine (901035A) and N,N-Dimethylbenzylamine (901035B)

In Example 1, sample containing 50 mg MAb1 was applied to N-benzyl-N-methyl ethanolamine immobilised on Sepharose™ 6 FF (901035A), N,N-dimethylbenzylamine immobilised on Sepharose™ 6 FF (901035B), and the reference matrix Q Sepharose™ FF in 25 mM Bis-Tris, 100 mM NaCl (~12 mS/cm), pH 6.5. Elution was carried out with 25 mM Bis-Tris, 0.5 M NaCl, pH 6.5.

Figure 2:
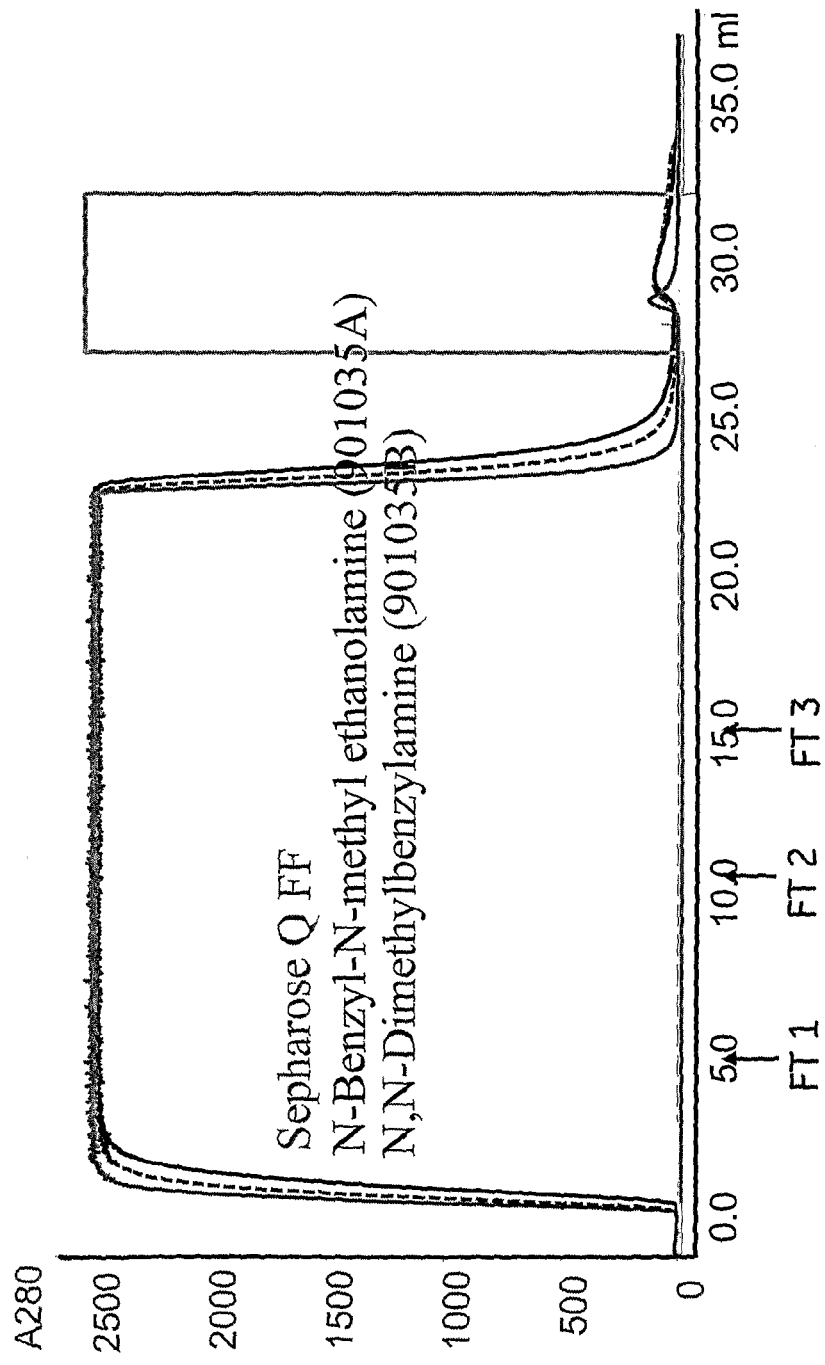
FIG. 2 shows a chromatogram of sample containing 50 mg Mab1 applied to multi-modal separation matrices comprising ligands of N-benzyl-N-methyl ethanolamine immobilised on Sepharose™ 6 FF (901035A); N,N-dimethylbenzylamine immobilised on Sepharose™ 6 FF (901035B); and Q Sepharose™ FF in 25 mM Bis-Tris, 100 mM NaCl (~12 mS/cm), pH 6.5. Elution was performed with 25 mM Bis-Tris, 0.5 M NaCl, pH 6.5.

The chromatograms of example 1 are shown in FIG. 2, which shows the two prototypes N-benzyl-N-methyl ethanolamine Sepharose™ 6 FF (901035A) and N,N-dimethylbenzylamine Sepharose™ 6 FF (901035B) compared to Q Sepharose™ FF. Flow-through (FT) fractions selected for analysis are indicated with arrows. The results for HCP and Protein A clearance shown in tables 2 and 3 below reveal that the prototypes are superior to Q Sepharose™ FF in that respect.

TABLE 2

Results from HCP analysis

| Column | pH | Start (ng/mL) | FT1 (ng/mL) | FT2 (ng/mL) | FT3 (ng/mL) |
|---|---|---|---|---|---|
| Q Sepharose ™ FF (ref) | 6.5 | 890 | 160 | 200 | 180 |
| N-benzyl-N-methylethanolamine, 146 μmol/mL (901035A) | 6.5 | 890 | 10 | 20 | 35 |
| N,N-dimethylbenzylamine 175 μmol/mL (901035B) | 6.5 | 890 | 27 | 39 | 45 |

TABLE 3

Results from PrA analysis

| Column | pH | Start (ng/mL) | FT1 (ng/mL) | FT2 (ng/mL) | FT3 (ng/mL) |
|---|---|---|---|---|---|
| Q Sepharose ™ FF (ref) | 6.5 | 0.40 | 0.69 | 0.46 | 0.31 |
| N-benzyl-N-methylethanolamine, 146 μmol/mL (901035A) | 6.5 | 0.40 | 0 | 0 | 0 |
| N,N-dimethylbenzylamine 175 μmol/mL (901035B) | 6.5 | 0.40 | 0.11 | 0.10 | 0.08 |

Example 2

MAb 1-Containing Sample Purified on Prototype Ligands Thiomicamine and 2-Aminobenzimidazole In this example, sample containing 20 mg MAb1 was loaded onto prototypes and reference separation matrices. Buffers were 25 mM Bis-Tris, 35 mM NaCl (~5 mS/cm), pH 6.5 for equilibration and loading. Elution buffer was 0.5 M Na-acetate, pH 4.0. a) Thiomicamine, 65 μmol/mL (1282004), b) Thiomicamine 128 μmol/mL (1282002), c) Q Sepharose™ FF, d) 2-aminobenzimidazole (ABI), 65 μmol/mL (1282045) and e) 2-aminobenzimidazole (ABI), 146 μmol/mL (1282032). The results for the HCP and Protein A analyses are shown below in tables 4 and 5.

TABLE 4

Results from HCP analysis

| Column | pH | Start (ng/mL) | FT1 (ng/mL) | FT2 (ng/mL) |
|---|---|---|---|---|
| Thiomicamine, 65 μmol/mL (1282004) | 6.5 | 351 | ≦10 | ≦10 |
| Q Sepharose ™ FF | 6.5 | 351 | 11 | 11 |
| 2-amino-benzimidazole (ABI), 65 μmol/mL (1282045) | 6.5 | 351 | ≦10 | ≦10 |

TABLE 5

Results from PrA analysis

| Column | pH | Start (ng/mL) | FT1 (ng/mL) | FT2 (ng/mL) |
|---|---|---|---|---|
| Thiomicamine, 65 μmol/mL(1282004) | 6.5 | 0.39 | 0.00 | 0.00 |
| Q Sepharose ™ FF | 6.5 | 0.39 | 0.09 | 0.21 |
| 2-aminobenzimidazole (ABI), 65 μmol/mL(1282045) | 6.5 | 0.39 | 0.00 | 0.00 |

Example 3

Figure 3A:
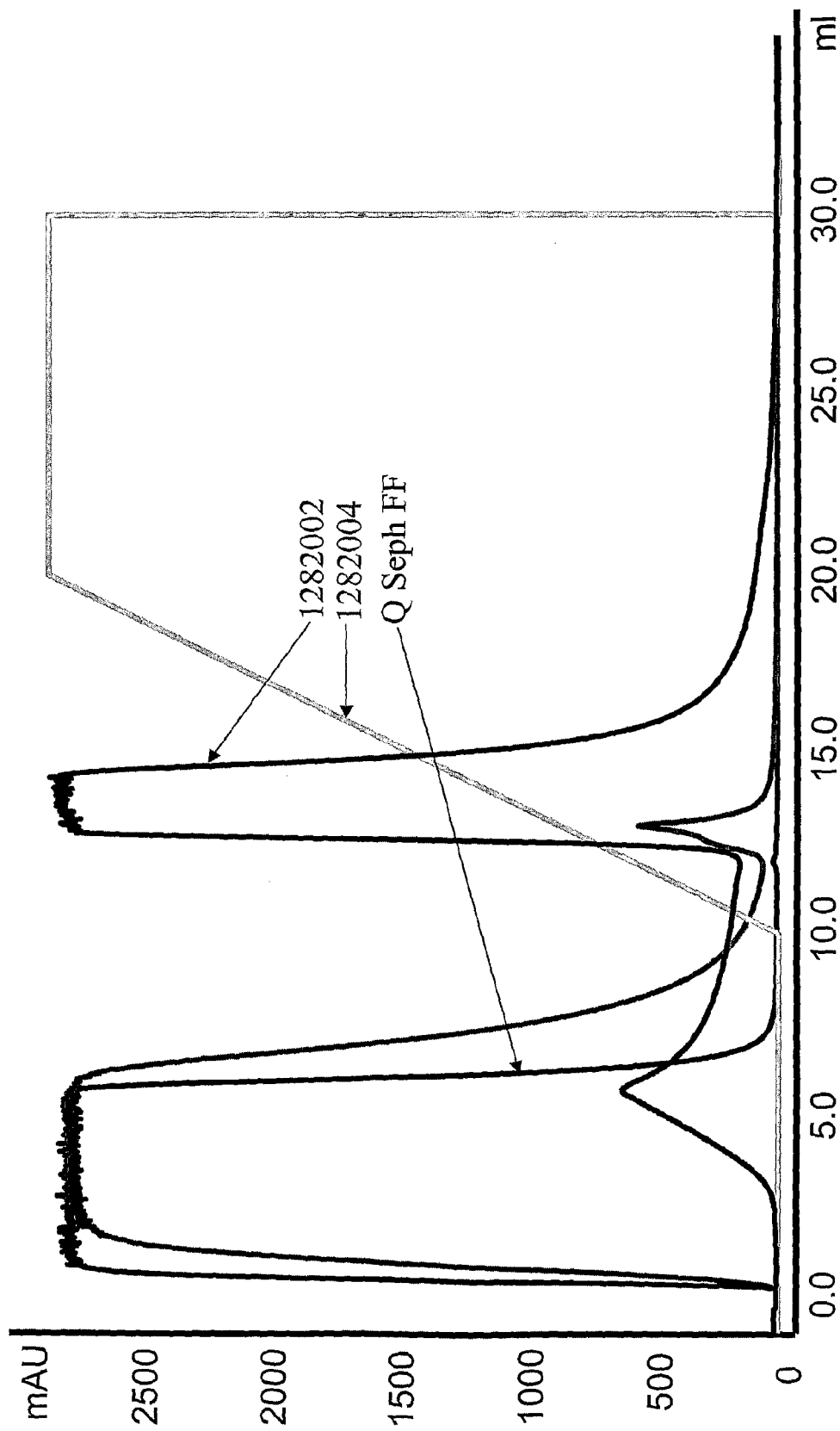
FIGS. 3a and 3b show chromatograms of sample containing 20 mg MAb 2, loaded onto prototypes and reference, as described in Example 3 below. Buffers were 25 mM Bis-Tris, 100 mM NaCl (~12 mS/cm), pH 6.0 for equilibration and loading. Elution buffer was 0.5 M Na-acetate, pH 4.0. 3a) thiomicamine (1282004), 65 µmol/mL, thiomicamine (1282002), 128 µmol/mL and Q Sepharose™ FF. b) 2-aminobenzimidazole (1282045), 65 µmol/mL, 2-aminobenzimidazole (1282032), 146 µmol/mL and Q Sepharose™ FF.
Figure 3:
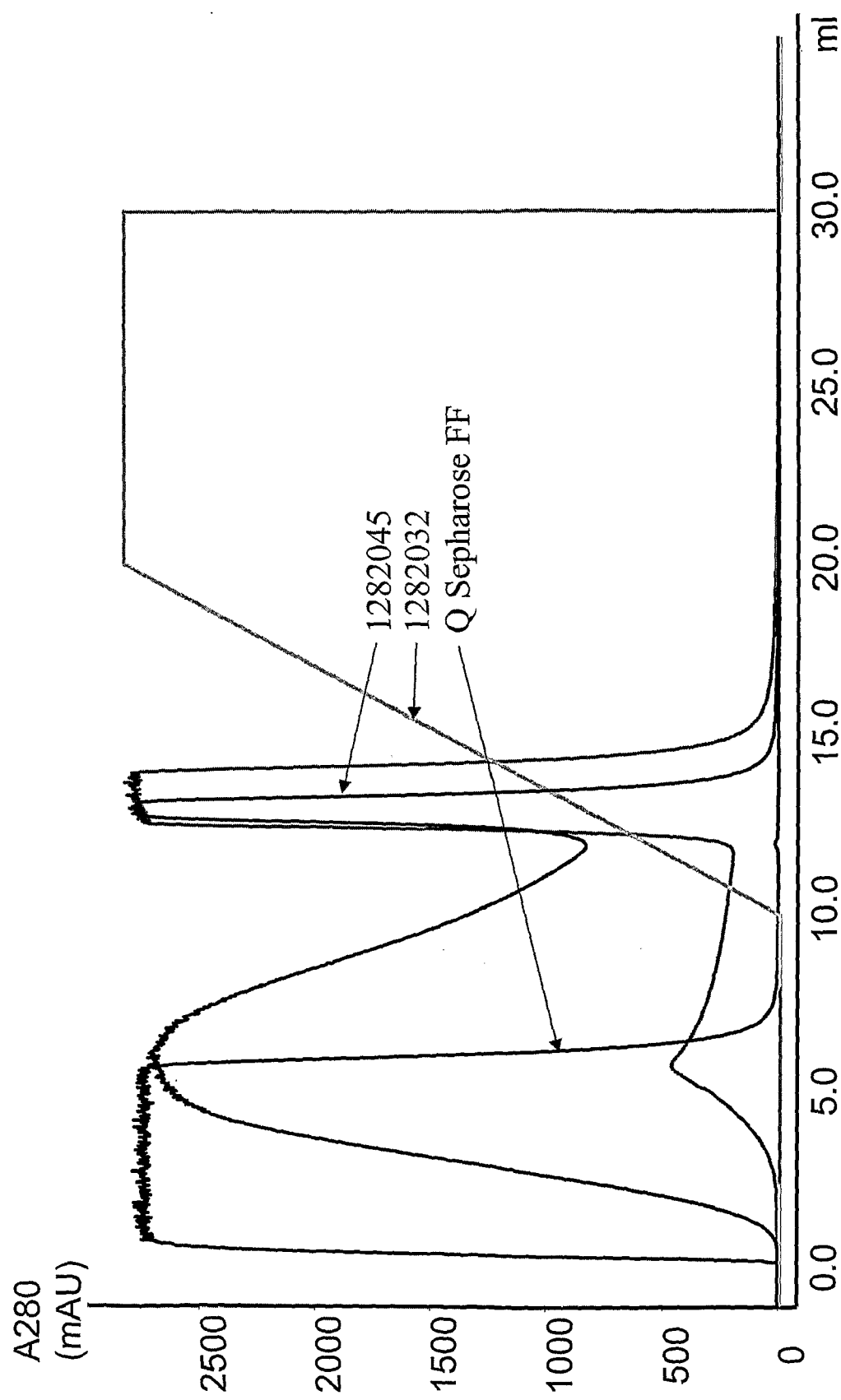

MAb2-Containing Sample Purified on Prototype Ligands Thiomicamine and 2-Aminobenzimidazole Sample containing 20 mg MAb2 was applied to prototypes and reference. Buffer was 25 mM Bis-Tris, 100 mM NaCl (~12 mS/cm), pH 6.0. Elution was performed with 0.5 M Na-acetate, pH 4.0. The resulting chromatograms are shown in FIG. 3. 3a) Thiomicamine (1282004), 65 μmol/mL, Thiomicamine (1282002), 128 μmol/mL and Q Sepharose™ FF. b) 2-aminobenzimidazole (1282045), 65 μmol/mL, 2-aminobenzimidazole (1282032), 146 μmol/mL and Q Sepharose™ FF. Analytical SEC was used to select fractions for the HCP and Protein A analyses as shown in tables 6 and 7 below.

TABLE 6

Results from HCP analysis

| Column | pH | Start (ng/mL) | FT1 (ng/mL) | FT2 (ng/mL) |
|---|---|---|---|---|
| Thiomicamine, 65 μmol/mL (1282004) | 6.0 | 170 | ≦10 | ≦10 |
| Q Sepharose™ FF | 6.0 | 170 | 66 | 55 |

TABLE 7

Results from PrA analysis

| Column | pH | Start (ng/mL) | FT1 (ng/mL) | FT2 (ng/mL) |
|---|---|---|---|---|
| Thiomicamine, 65 μmol/mL (1282004) | 6.0 | 5.42 | 0.00 | 0.24 |
| Q Sepharose™ FF | 6.0 | 5.42 | 3.90 | 4.93 |

Example 4

Purification of MAb1 from a Sample Comprising MAb1 and Recombinant Protein a (rPrA) on Prototype Ligands N-Benzyl-N-Methylethanolamine, N,N-Dimethylbenzylamine, Thiomicamine and 2-Aminobenzimidazole In this example, chromatography on prototypes with a sample containing mAb1-rProtein A was performed. A-buffer was 25 mM Bis-Tris, 50 mM NaCl, pH 6.0. The conductivity was approximately 7 mS/cm. B-buffer was 0.5 M Na-Acetate, pH 4.0. The flow rate was 0.5 mL/min (150 cm/h). Sample was 10 mg mAb1, 0.10 mg rPrA at a concentration of 4 mg/ml mAb1 and 1% rProtein A (w/w). The results are shown in FIG. 4.

Figure 4A:
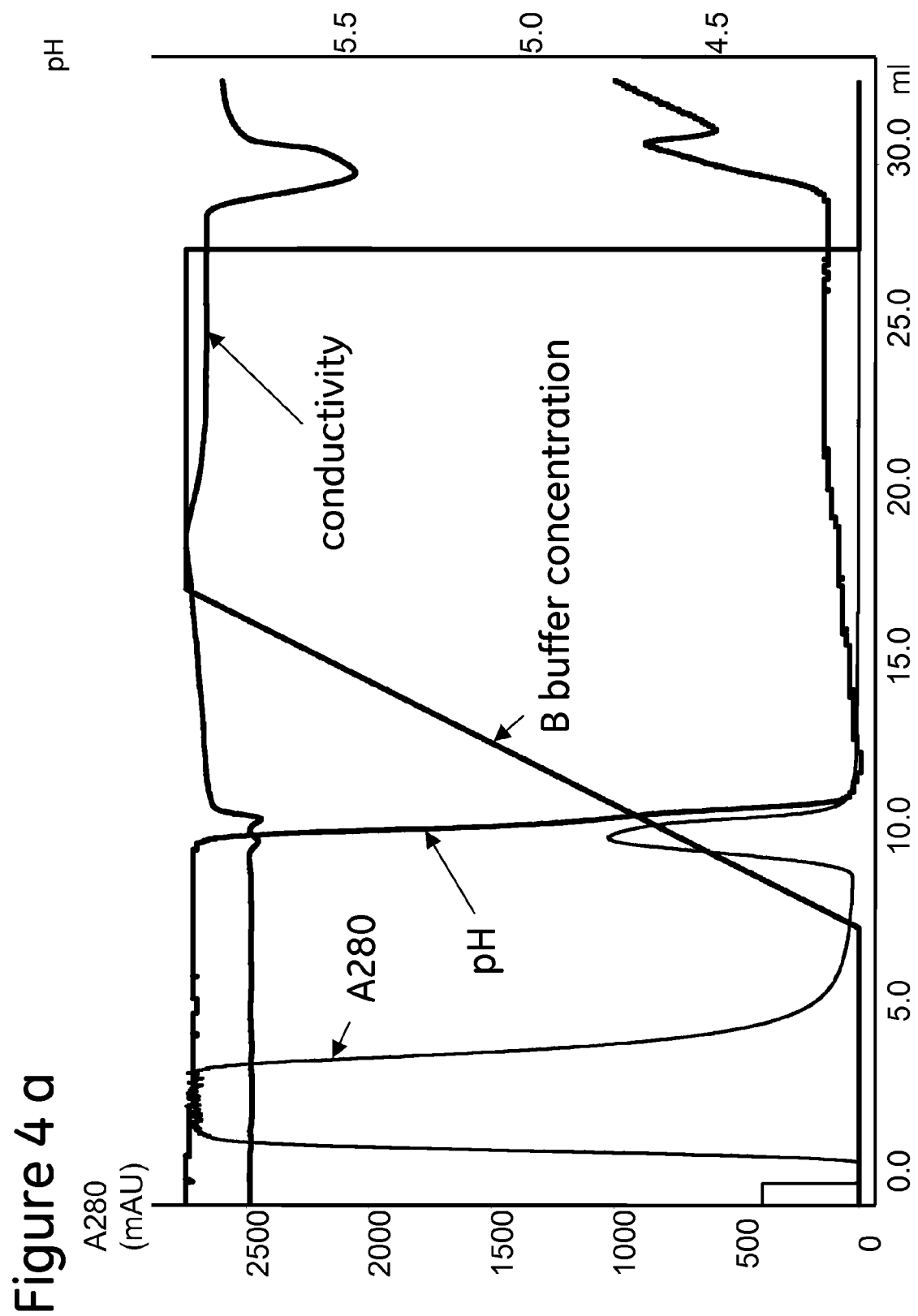
FIGS. 4a-4g show the results of chromatography carried out on prototypes with mAb1-rProtein A. A-buffer was 25 mM Bis-Tris, 50 mM NaCl, pH 6.0. The conductivity was approximately 7 mS/cm. B-buffer, 0.5 M Na-Acetate, pH 4.0, was used for elution. Flow rate was 0.5 mL/mm (150 cm/h). Sample was 10 mg mAb1, 0.10 mg rPrA at a concentration of 4 mg/ml mAb1 and 100 rProtein A (w/w).
Figure 4:
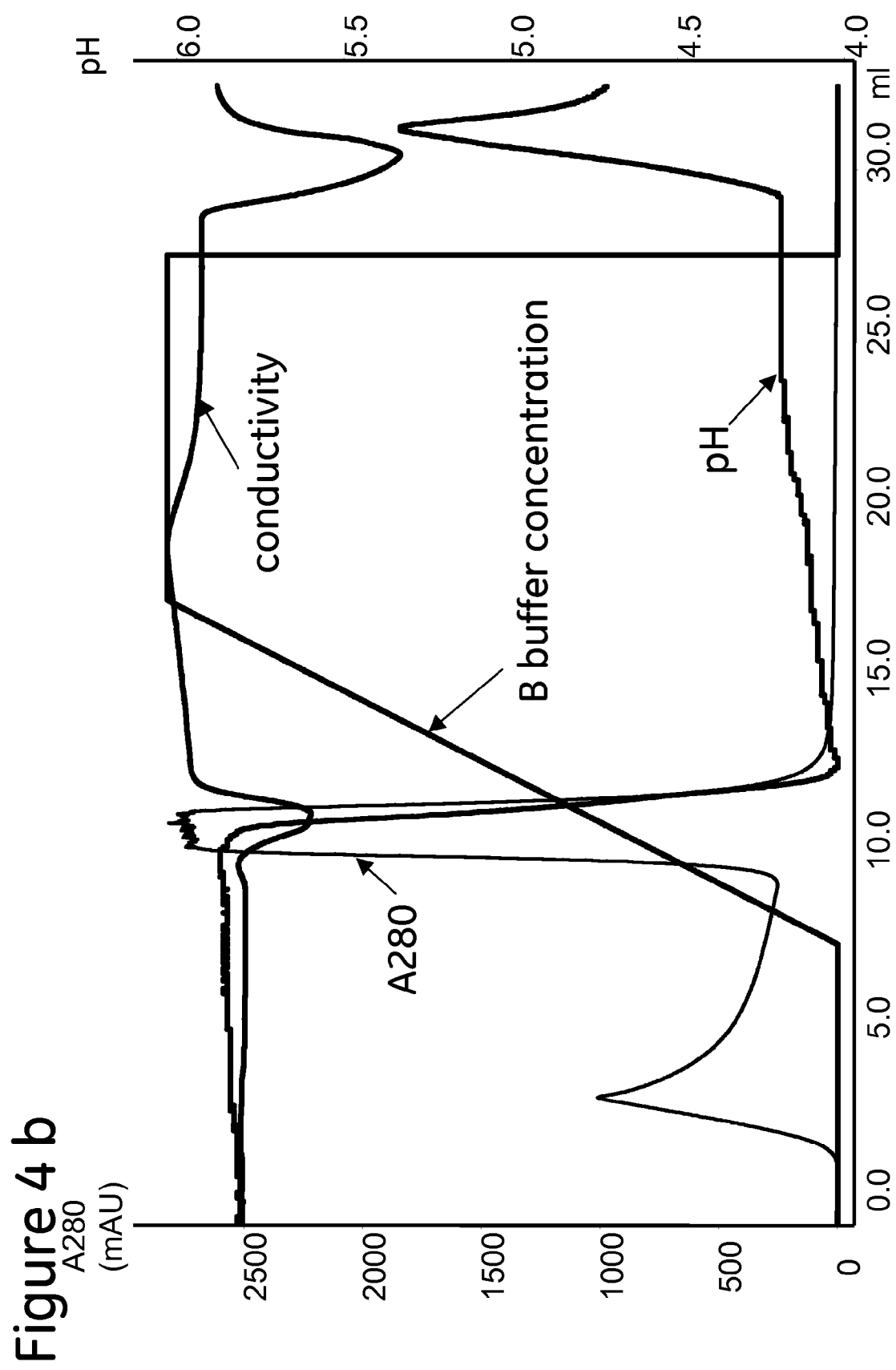
Figure 4:
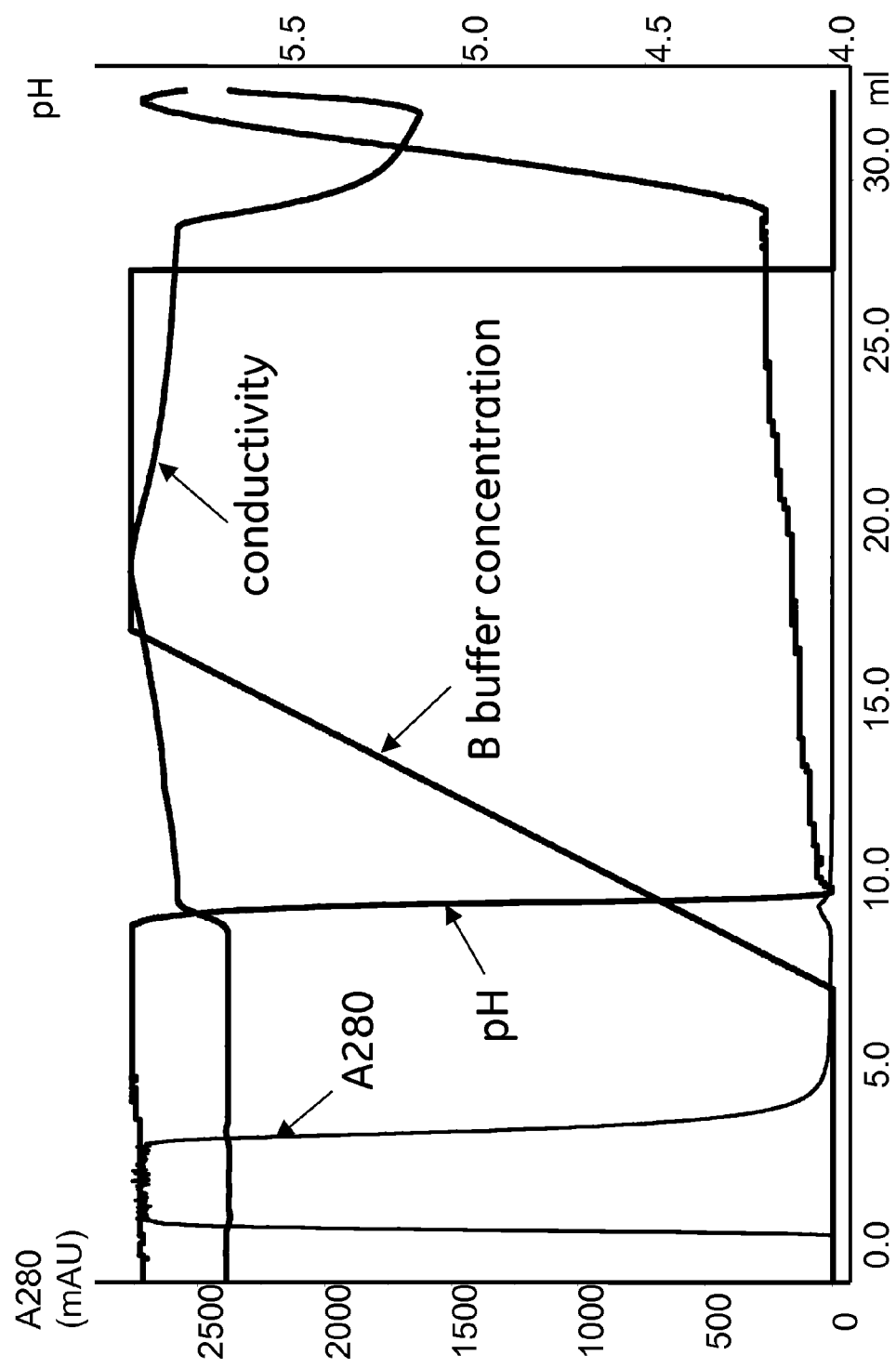
Figure 4:
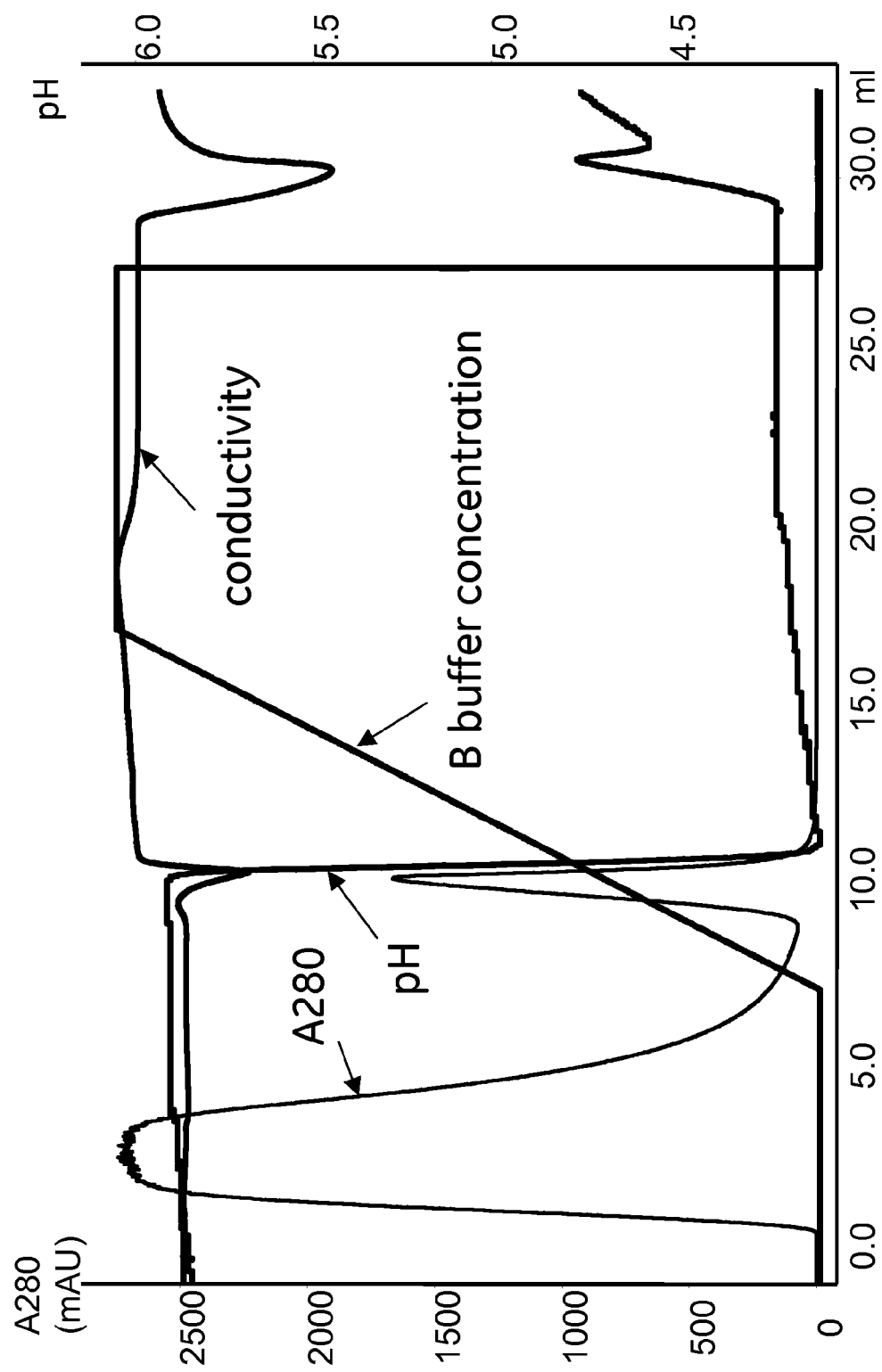
Figure 4:
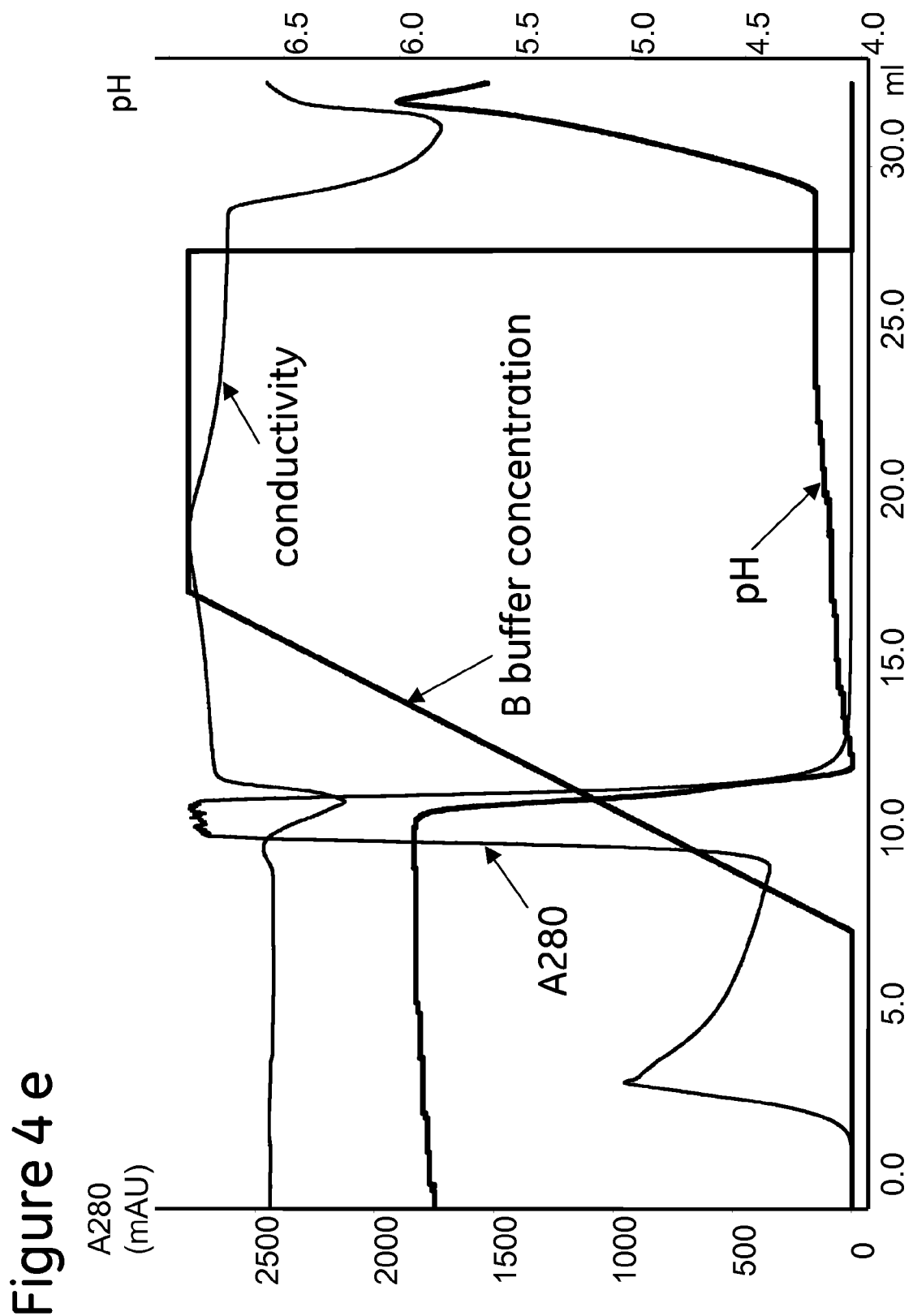
Figure 4F:
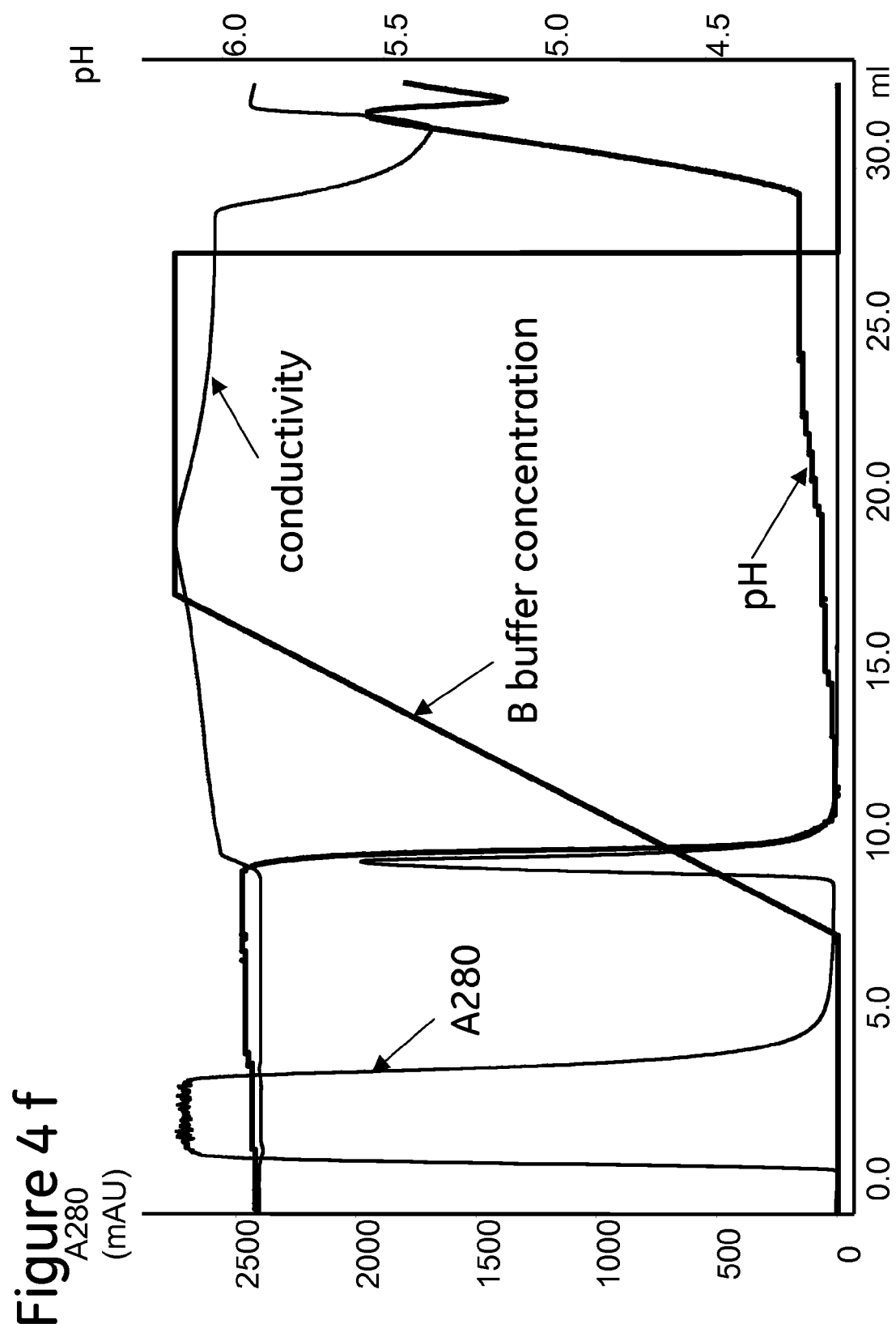
Figure 4:
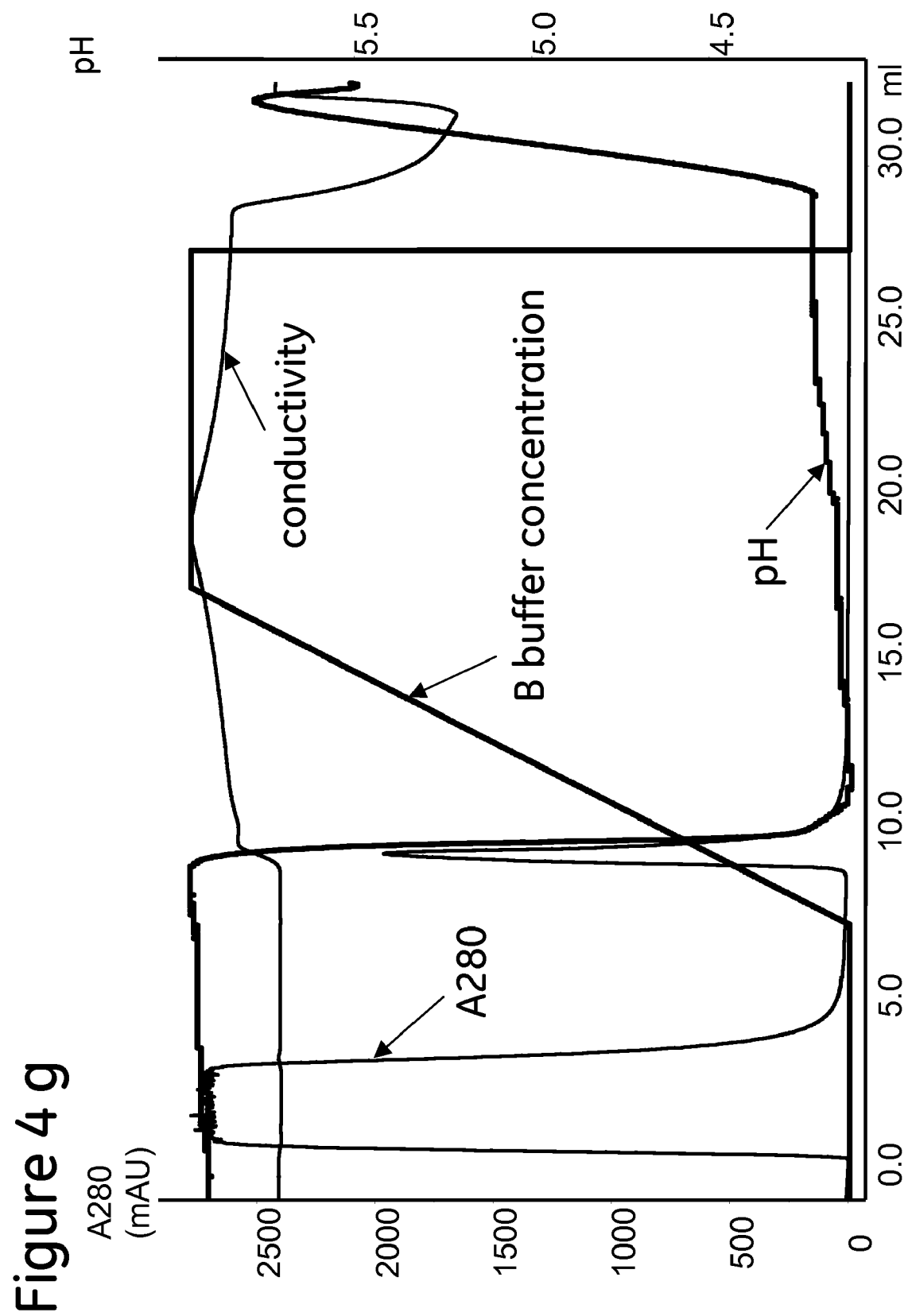
Figure 5:
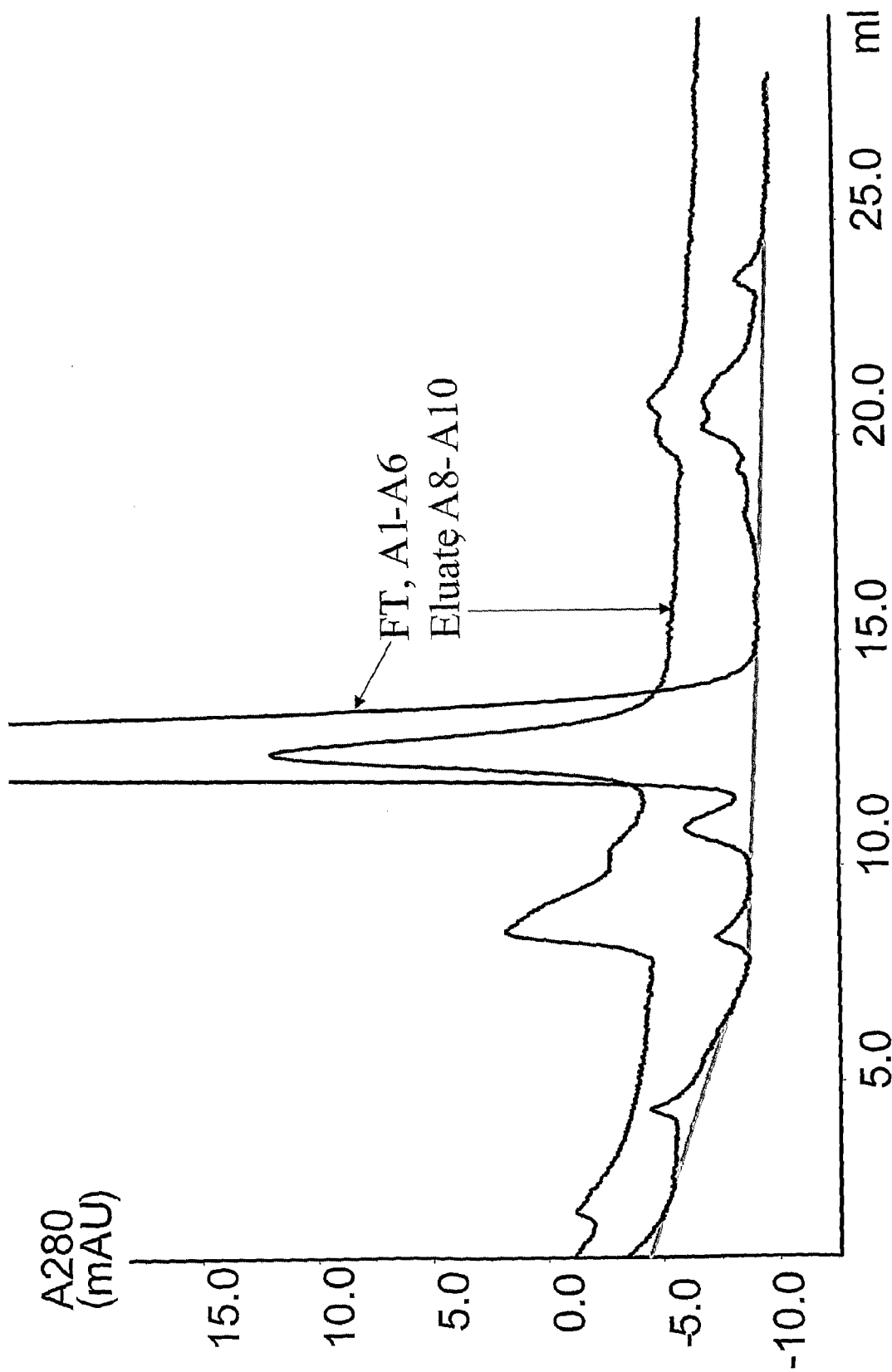
Figure 5C:
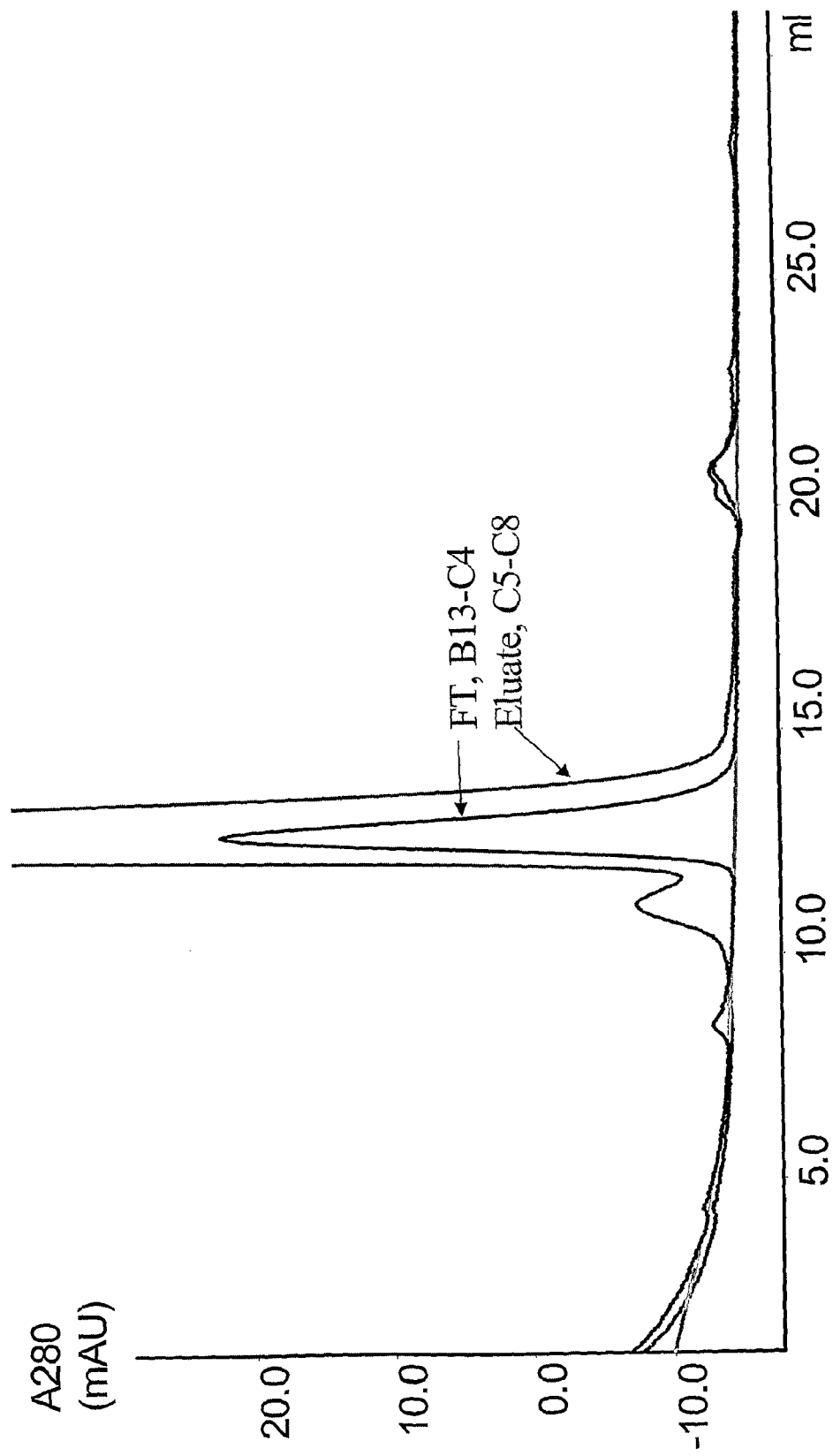
Figure 5:
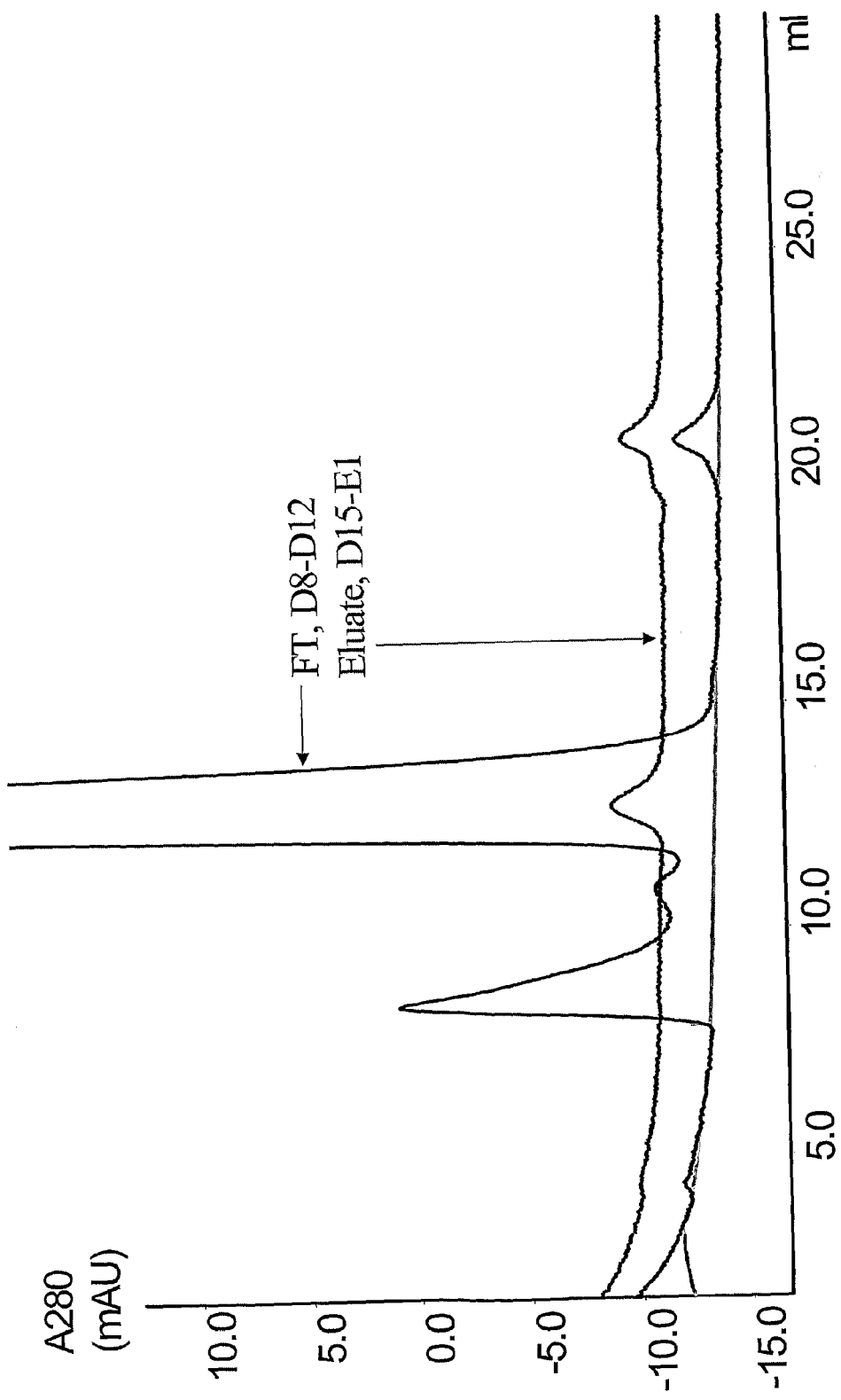
Figure 5F:
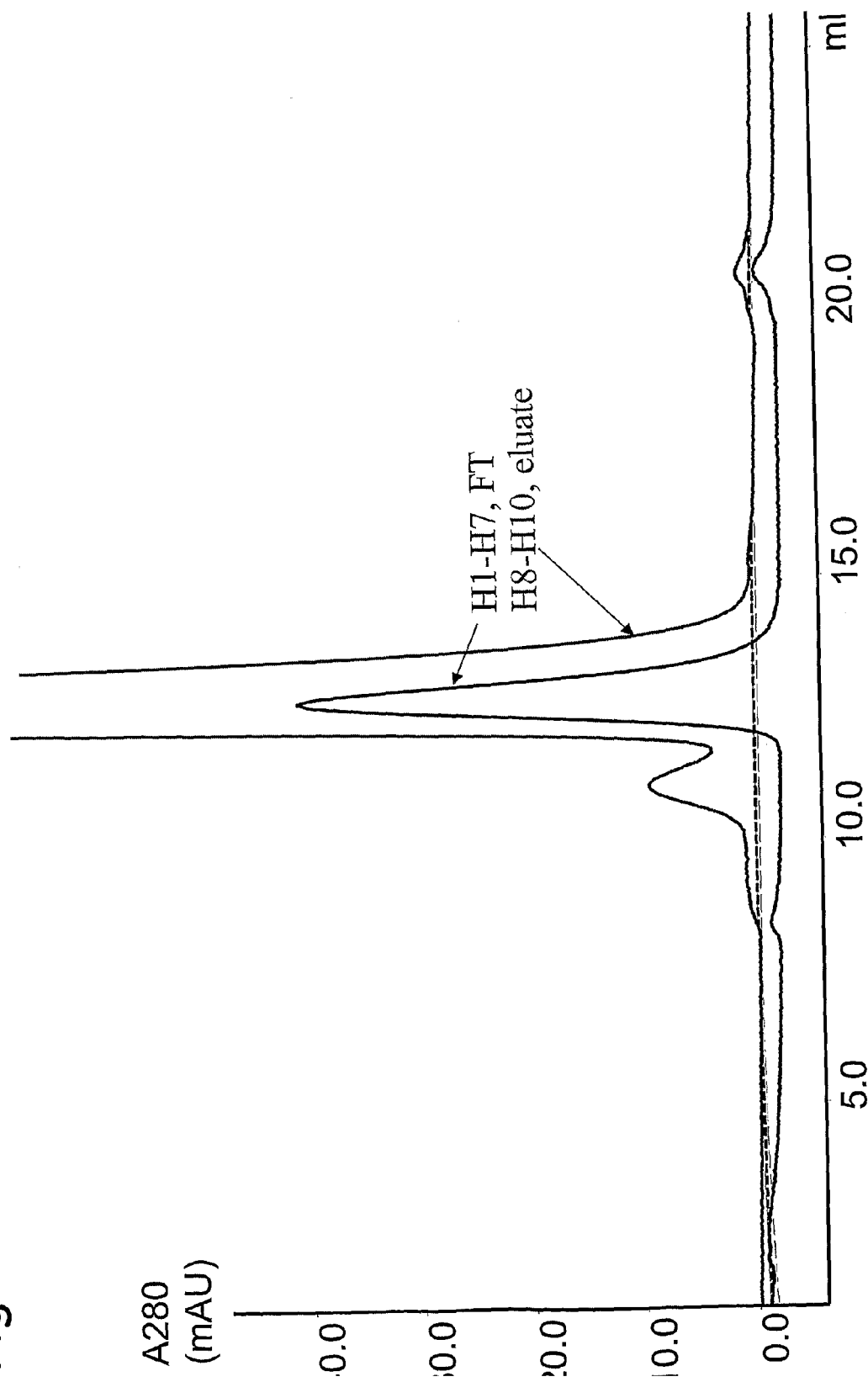
Figure 5:
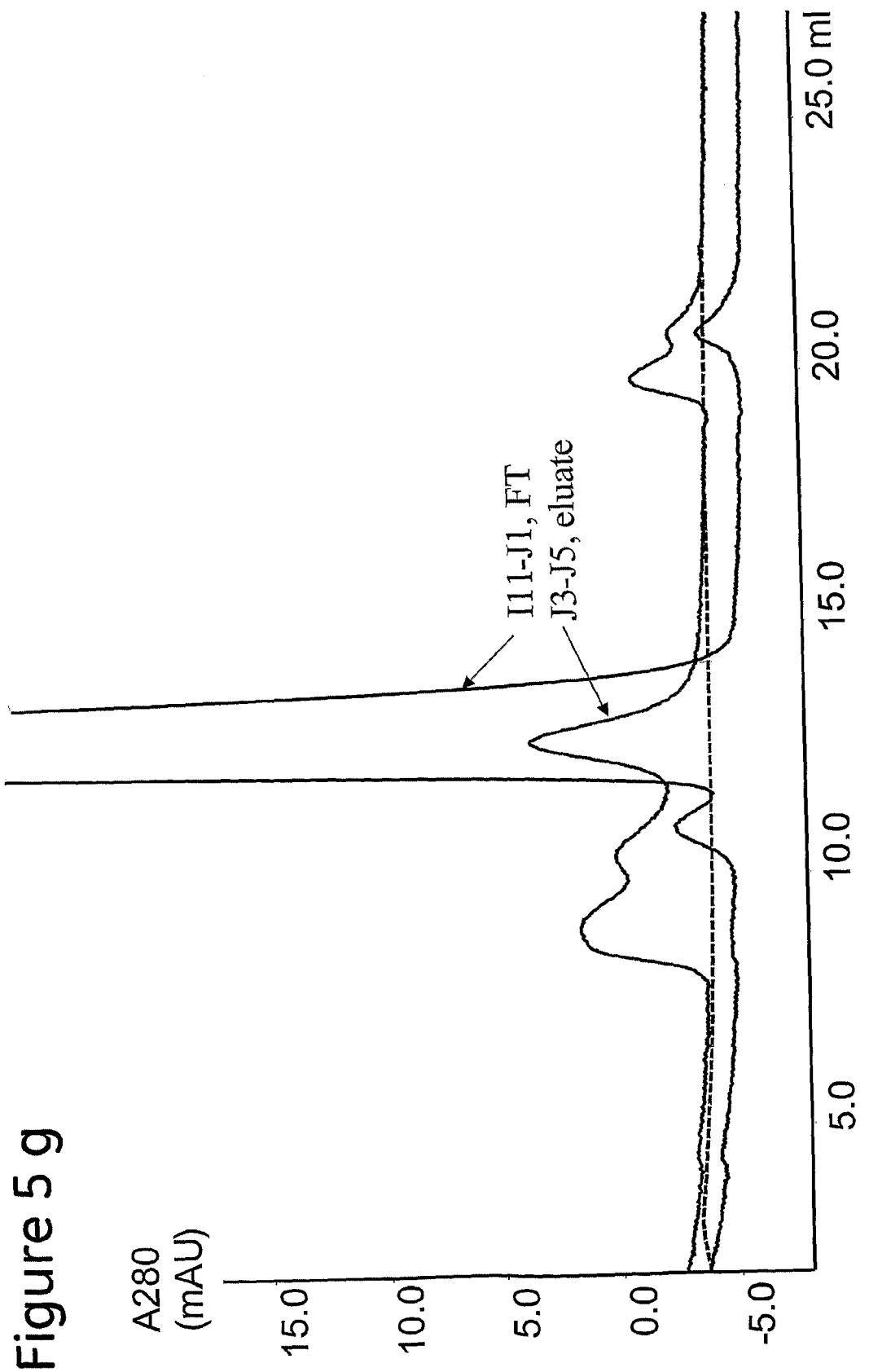
Figure 5:
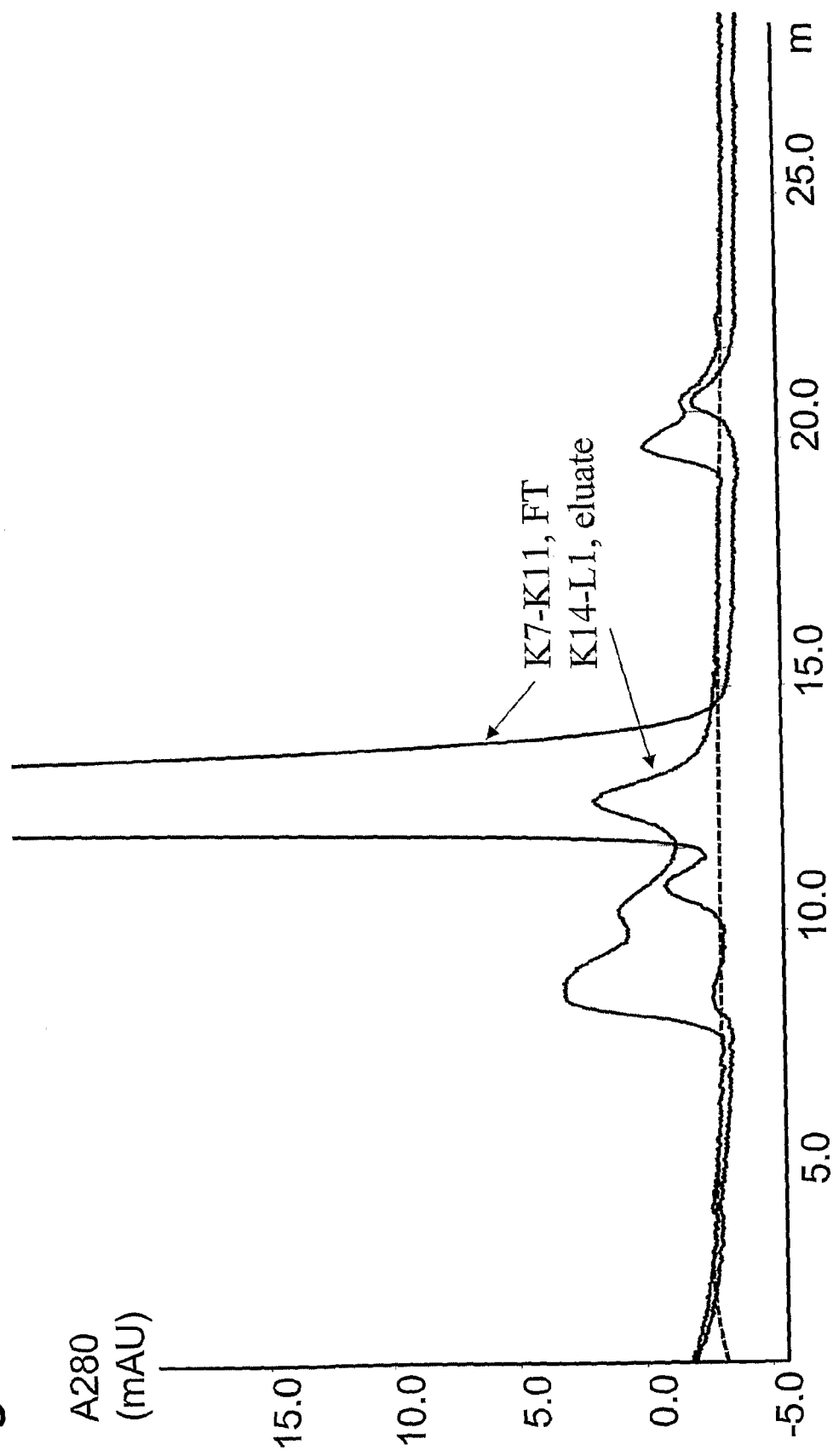

Finally, analytical SEC on sample with mAb 1, 1% rPrA and pooled flow-through and eluate fractions from the chromatographic runs in FIG. 4 were performed. The results are shown in FIG. 5. In FIG. 5 a, the shaded peak is the complex of MAb 1-Protein A.

Example 5

Antibody Purification on Q Phenyl Sepharose 6 Fast Flow Disposition

Under non-binding conditions, sample containing approximately 50 mg mAb were loaded onto prototype Q Phenyl Sepharose™ 6 Fast Flow. Flow-through fractions (FT) were collected at 5, 10 and 15 column volumes (CV). Fractions from the elution peak were analysed.

Q Phenyl Sepharose™ 6 Fast Flow was made by attaching Q-groups (—N(CH$_3$)$_3$) to Phenyl Sepharose™ 6 Fast Flow (45 μmol Phenyl groups/ml gel) in accordance with standard procedure (see below). The ion exchange capacity of Q Phenyl Sepharose™ 6 Fast Flow was 108 μmol/ml gel. At pH 7.0 or 8.0, sample containing 50 mg mAb (MabSelect purified) were loaded into the column and the performance of Q Phenyl Sepharose™ 6 Fast Flow was evaluated by analyzing selected flow-through fractions with respect of host cell proteins (HCP) and Protein A content Materials/Investigated Units Columns and Phenyl Sepharose™ 6 Fast Flow were obtained from GE Healthcare, Uppsala, Sweden

| HR 5/5 ™ | cat.no. 18-0338-01 | CV = 1 mL |

Instruments

| Chromatography systems: | ÄKTAExplorer ™ 10 |
| Spectrophotometer | Spectra MAX plus |

Chemicals

All chemicals used were of analytical grade. Water was MilliQ-filtered.

Preparation of Q Phenyl Sepharose™ 6 Fast Flow

One way to prepare a separation matrix according to the invention is exemplified below, starting from a crosslinked agarose gel (Phenyl Sepharose™ 6 Fast Flow (high sub), GE Healthcare, Uppsala, Sweden).

Introduction of Q Group on Phenyl Sepharose™ 6 Fast Flow (High Sub):

Q-groups (—N(CH$_3$)$_3$) were introduced on Phenyl Sepharose™ 6 Fast Flow (high sub) via reaction with glycidyl trimethylammonium chloride (G-MAC) as follows: 15 g of suction dried Phenyl Sepharose™ 6 Fast Flow (high sub) was mixed with 5 ml of water, 5 ml of 50% aqueous solution of NaOH, 0.02 g of NaBH$_4$, and 40 ml of G-MAC. The mixture was stirred for 16 hour at 30° C. After filtration of the mixture, the gel was washed successively, with 100 ml distilled water, 100 ml ethanol, and 100 ml distilled water. Titration gave a degree of substitution of 0.11 mmol amines/ml gel.

Samples

The monoclonal antibody used were expressed in a CHO cultures and subsequently purified using conventional Protein A affinity chromatography prior to the present experiments.

Concentration Determination of mAb

The mAb sample was diluted ten times with buffer. Two replicates of the sample solution were measured at A280. The average value was used to calculate the concentration according to Lambert Beer's law:

$$C=A/(l\times\varepsilon)$$

C concentration of IgG
A=absorbance at 280 nm
l=path length
ε=molar extinction coefficient for the mAb, mg$^{-1}$ ml=1.46

Chromatography on Q Phenyl Sepharose™ 6 Fast Flow

The separation of mAb from host cell proteins and protein A was tested under non-binding conditions. The sample applied to the columns was MabSelect purified mAb1. The flow rate was 0.5 ml/min (150 cm/h). The absorbance at 280 nm was detected during all runs. Two different buffers (see below) were tested. A buffer exchange to A-buffer was performed before each run. HiPrep desalting and HiTrap desalting columns were used depending on the sample volume.

Buffers: A-buffer: 25 mM Tris/HCl pH 8.0
B-buffer: 25 mM Tris/HCl, 0.5 M NaCl, pH 8.0
A-buffer: 25 mM Phosphate buffer pH 7.0
B-buffer: 25 mM Phosphate buffer, 0.5 M NaCl, pH 7.0

Method: pH adjusted eluate from MabSelect was used as start material.

| | |
|---|---|
| Equilibration | 5 CV A-buffer |
| Sample injection | 16 CV (50 mg mAb) |
| Wash | 5 CV A-buffer |
| Gradient | 5 CV 100% B-buffer |
| Clean after gradient | 5 CV A-buffer |

1 ml fractions were collected during sample injection, wash and elution

CIP (cleaning in place) with 1 M NaOH was performed after each run. The residence time was approximately 25 minutes.

Protein A Analysis

Selected fractions were mixed with SPA sample diluent in proportions of 800 µl SPA sample diluent+200 µl sample. After mixing, the fractions were heated on a heating block at 99° C. for 10 minutes, and then mixed again. The samples were then analysed for recombinant Protein A.

Host Cell Proteins (HCP) Analysis

The samples (min. 600 µl) were analysed for HCP content. The lower detection limit is 10 ng/nL.

Results

Figure 6:
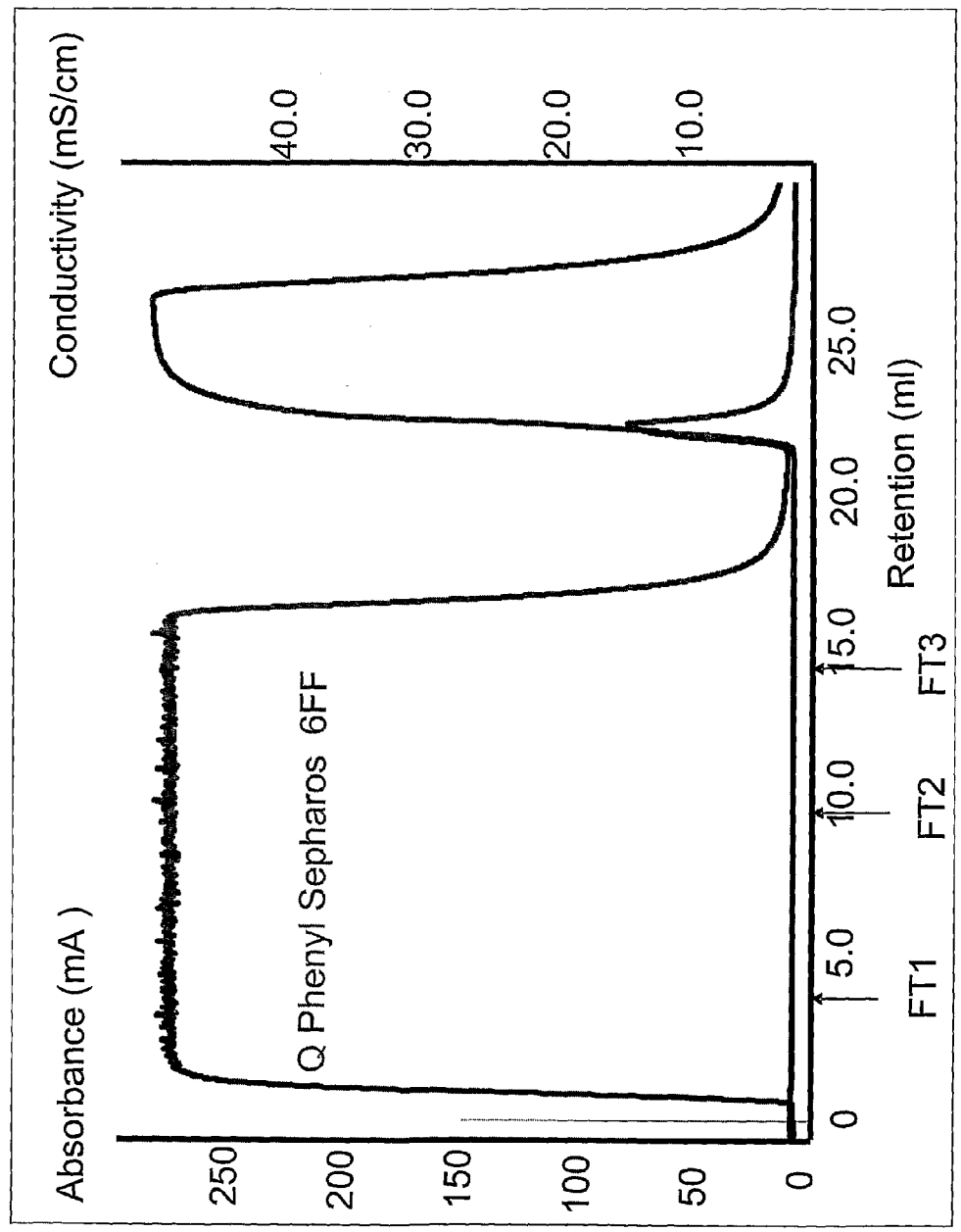
FIG. 6 shows the results from Example 5 below. More specifically, the chromatogram resulting from sample containing 50 mg Mab applied to Q Phenyl Sepharose™ 6 Fast Flow is shown. Elution was performed with 25 mM Tris, 0.5 M NaCl, pH 8.0. It appears from FIG. 6 how the monoclonal antibody molecules are not adsorbed to Q Phenyl Sepharose™ Fast Flow, since only a very small peak is observed in the chromatogram at the gradient elution.

Under non-binding conditions, approximately 50 mg mAb were loaded onto a HR 5/5 column packed with Q Phenyl Sepharose™ Fast Flow at two different pH:s (pH 7.0 and 8.0). Flow-through fractions were collected at 5, 10 and 15 column volumes (CV) according to FIG. 1. Table 8 and 9 present the results from protein A and HCP analysis of the flow-through fractions. No rests of protein A could be detected in the fractions. Furthermore, no host cell proteins could be detected in FT1 and FT2 when a sample pH of 8.0 was used. Small amounts of host cell proteins were observed when a sample pH of 7.0 was used but the reduction in HCP was about 50 times compared to the HCP-content in the sample. FIG. 6 also shows that the monoclonal antibody molecules are not adsorbed to Q Phenyl Sepharose™ Fast Flow since only a very small peak is observed in the chromatogram at the gradient elution (FIG. 6).

TABLE 8

Results from protein A analysis.

| Column | pH | Start (ng/ml) | FT1 (ng/ml) | FT3 (ng/ml) | Eluate (ng/ml) |
|---|---|---|---|---|---|
| Q Phenyl Sepharose ™ FF | 8.0 | 6.98 | 0.00 | 0.00 | 48.25 |
| Q Phenyl Sepharose ™ FF | 7.0 | 5.03 | 0.00 | 0.00 | 36.15 |

The sample volume was 16 ml and the FT1-FT3 were 1 ml fractions. The pooled elution volumes were 2 ml.

TABLE 9

Results from host cell proteins analysis.

| Column | pH | Start (ng/ml) | FT1 (ng/ml) | FT2 (ng/ml) | FT3 (ng/ml) | Eluate (ng/ml) |
|---|---|---|---|---|---|---|
| Q Phenyl Sepharose ™ FF | 8.0 | 1100 | <10 | <10 | 12 | 4900 |
| Q Phenyl Sepharose ™ FF | 7.0 | 1200 | 16 | 23 | 26 | 5100 |

The sample volume was 16 ml and FT1-FT3 were 1 ml fractions. The pooled elution volumes were 2 ml.

The invention claimed is:

1. A method for separating one or more antibodies from one or more other compounds in a liquid sample, which method comprises contacting a mobile phase comprising said liquid sample with a multi-modal separation matrix to adsorb one or more of said other compounds while the antibodies remain free in the mobile phase, wherein the multi-modal separation matrix comprises first groups capable of interacting with negatively charged sites of said other compound(s) and second groups capable of at least one interaction other than charge-charge interaction with said other compound(s).

2. The method of claim 1, wherein the multi-modal separation matrix is provided in a chromatography column, the mobile phase is passed through said column by gravity and/or pumping, and the antibodies are recovered in the flow-through of the column.

3. The method of claim 1, wherein the liquid sample comprises a supernatant obtained from cell fermentation.

4. The method of claim 1, wherein the contact with the multi-modal separation matrix is preceded by a step of mechanical filtration and/or chromatography.

5. The method of claim 4, wherein the liquid sample comprises an eluate from a separation matrix.

6. The method of claim 5, wherein the separation matrix from which the eluate is obtained comprises protein ligands.

7. The method of claim 5, wherein the separation matrix from which the eluate is obtained comprises protein A or G ligands.

8. The method of claim 1, wherein the liquid sample comprises a crude feed.

9. The method of claim 8, wherein the other compound(s) are host cell proteins and substantially all said proteins are adsorbed to the multi-modal separation matrix.

10. The method of claim 1, wherein the conductivity of the mobile phase is in the range of 0-25 mS/cm.

11. The method of claim 1, wherein the first groups are quaternary amines.

12. The method of claim 1, wherein the second groups are hydrogen-bonding groups.

13. The method of claim 1, wherein the second groups are hydrophobic groups.

14. The method of claim 1, wherein the separation matrix comprises first and second groups coupled to same ligands which are immobilized on said matrix.

15. The method of claim 14, wherein the first and second group are distanced from each other by a hydrocarbon chain of 1-3 carbon atoms.

16. The method of claim 1, wherein ligands have been immobilised to a support of said separation matrix via said first groups.

17. The method of claim 1, wherein the separation matrix comprises first and second groups coupled to different ligands which are immobilized on said matrix.

18. The method of claim 1, wherein the separation matrix is particulate and comprises a mixture of first particles, to which ligands comprising the first groups have been immobilised; and second particles, to which ligands comprising the second groups have been immobilised.

19. The method of claim 1, wherein the separation matrix is a filter to which a mixture of first ligands comprising the first groups; and second ligands comprising the second groups have been immobilised.

20. The method of claim 1, wherein the separation matrix comprises third groups capable of a third interaction with one said other compound.

21. The method of claim 1, wherein the antibodies are monoclonal antibodies.

22. The method of claim 21, wherein the antibodies are humanised antibodies.

23. The method of claim 1, wherein the multi-modal separation matrix is provided in a disposable chromatography column.

24. The method of claim 23, wherein the disposable column is sterilised prior to contacting the mobile phase.

25. The method of claim 1, wherein the second groups comprise aromatic or heteroaromatic ring structure(s).

\* \* \* \* \*